United States Patent [19]

Stevenson

[11] Patent Number: 5,116,850
[45] Date of Patent: May 26, 1992

[54] HETEROCYCLIC PYRAZOLINE CARBOXANILIDES

[75] Inventor: Thomas M. Stevenson, Newark, Del.

[73] Assignee: E. I. Du Pont de Nemours and Co., Wilmington, Del.

[21] Appl. No.: 543,855

[22] PCT Filed: Nov. 30, 1988

[86] PCT No.: PCT/US88/04218
§ 371 Date: May 21, 1990
§ 102(e) Date: May 21, 1990

[87] PCT Pub. No.: WO89/05300
PCT Pub. Date: Jun. 15, 1989

Related U.S. Application Data

[63] Continuation of Ser. No. 126,619, Nov. 30, 1987, abandoned.

[51] Int. Cl.⁵ ................ A61K 31/44; C07D 401/04

[52] U.S. Cl. .................... 514/341; 514/247; 514/403; 514/255; 514/256; 514/365; 514/374; 514/397; 546/279; 548/379; 548/236; 548/204; 548/336; 544/238; 544/333; 544/405

[58] Field of Search ............. 546/279; 514/341

[56] References Cited

U.S. PATENT DOCUMENTS

| | | | |
|---|---|---|---|
| 4,070,365 | 1/1978 | Van Daalen et al. | 548/379 |
| 4,174,393 | 11/1979 | Van Daalen et al. | 548/379 |
| 4,767,779 | 8/1988 | Duggan | 548/379 |
| 4,837,220 | 6/1989 | Neh et al. | 548/379 |
| 4,888,340 | 12/1989 | Neh et al. | 548/379 |

FOREIGN PATENT DOCUMENTS 0153127  8/1985  European Pat. Off.

OTHER PUBLICATIONS

Vaughan Jan. Org. Chem. vol. 20, 1955, pp. 1619-1926.

Primary Examiner—Jane T. Fan
Attorney, Agent, or Firm—James A. Costello

[57] ABSTRACT

Heterocyclic pyrazoline carboxanilide insecticides including all geometric and stereoisomers thereof, as well as agricultural compositions containing them.

13 Claims, No Drawings

HETEROCYCLIC PYRAZOLINE CARBOXANILIDES

This is a continuation of Ser. No. 126,619 filed Nov. 30, 1987, now abandoned.

BACKGROUND OF THE INVENTION

Compounds and compositions comprising heterocyclic pyrazoline carboxanilides having a $>N-N=C-C(O \text{ or } S)-N<$ backbone.

*J. Org. Chem.*, 20, page 1619 (1955) discloses 1,5-diphenyl-2-pyrazoline-3-carboxamide. No utility is presented. Harhash et al., *J. Heterocyclic Chem.*, 21, page 1013 (1984), disclose the preparation of these five pyrazolines for which no utility is presented:

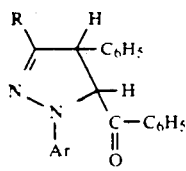

where R/Ar are $C_6H_5/C_6H_5$, $CO_2C_2H_5/C_6H_5$, $C(O)NHC_6H_5/C_6H_5$, $CH=CHC_6H_5/C_6H_5$ and $CH_3/4-NO_2-C_6H_4$.

U.S. Pat. No. 4,070,365 discloses insecticidal compounds of the formula

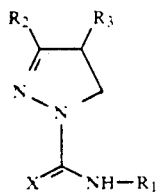

where $R_1$ is optionally substituted phenyl; $R_2$ and $R_3$ are independently optionally substituted pyridyl, thienyl or phenyl groups and X is O or S.

EPA 0153127 discloses insecticidal compounds of the formula

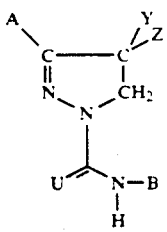

wherein A and B are unsubstituted or substituted aryl; U is O, S or NR; Y is alkyl, carbonyl or unsubstituted or substituted aryl, and Z is cycloalkyl or an unsubstituted or substituted aryl group.

PCT International Publication No. WO88/05046 discloses pyrazoline insecticides of the formula

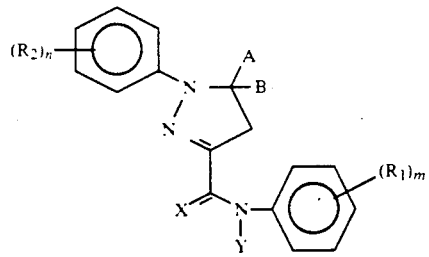

wherein:

A is H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$ or $C(S)SR_3$;

B is H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_2$ to $C_6$ alkenyl, $C_2$ to $C_6$ alkynyl, $C_2$ to $C_6$ alkoxycarbonyl, phenyl, phenyl substituted with 1 to 3 substituents independently selected from W, benzyl or benzyl substituted with 1 to 3 substituents independently selected from W.

SUMMARY OF THE INVENTION

This invention pertains to compounds of Formula I, including all geometric and stereoisomers thereof, agriculturally suitable salts thereof, agricultural compositions containing said compounds and salts, and their use as insecticides:

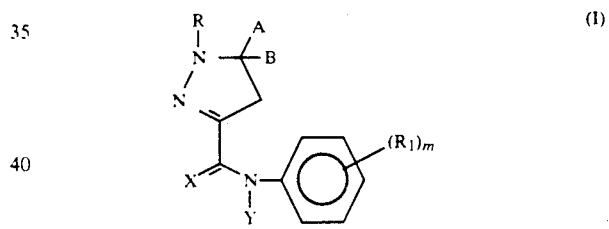

wherein:

X is O or S;

Y is selected from the group H, $C_1$ to $C_4$ alkyl, $C_2$ to $C_4$ alkoxyalkyl, $C_1$ to $C_4$ alkylthio, $C_1$ to $C_4$ haloalkylthio, SX', phenylthio, or phenylthio substituted with 1 to 3 substituents independently selected from W, $C_2$ to $C_4$ alkoxycarbonyl, C(O)H, $C_2$ to $C_4$ alkylcarbonyl and $C_2$ to $C_4$ haloalkylcarbonyl;

A is selected from the group H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$, $C(S)SR_3$ and J;

B is selected from the group H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_2$ to $C_6$ alkenyl, $C_2$ to $C_6$ alkynyl, $C_2$ to $C_6$ alkoxycarbonyl, phenyl, phenyl substituted with 1 to 3 substituents independently selected from W, benzyl and benzyl substituted with 1 to 3 substituents independently selected from W;

W is selected from the group halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl and $C_1$ to $C_2$ haloalkylsulfonyl;

R is

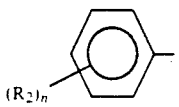

or K, being K when A is other than J;

$R_1$, $R_2$ and $R_5$ are independently selected from the group $R_3$, halogen, CN, $N_3$, SCN, $NO_2$, $OR_3$, $SR_3$, $S(O)R_3$, $S(O)_2R_3$, $OC(O)R_3$, $OS(O)_2R_3$, $CO_2R_3$, $C(O)R_3$, $C(O)NR_3R_4$, $S(O)_2NR_3R_4$, $NR_3R_4$, $NR_4C(O)R_3$, $OC(O)NHR_3$, $NR_4C(O)NHR_3$, $NR_4S(O)_2R_3$, and when m, n or p is 2, $R_1$, $R_2$ or $R_5$ can be taken together as —$OCH_2O$—, —$OCF_2O$—, —$OCH_2CH_2O$—, —$CH_2C(CH_3)_2O$—, —$OCF_2CF_2O$—, or —$CF_2CF_2O$— to form a 5- or 6-membered ring;

$R_3$ is selected from the group H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, $C_2$ to $C_4$ haloalkynyl, $C_2$ to $C_4$ alkoxyalkyl, $C_2$ to $C_4$ alkylthioalkyl, $C_1$ to $C_4$ nitroalkyl, $C_1$ to $C_4$ cyanoalkyl, $C_3$ to $C_6$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H or $C_1$ to $C_4$ alkyl, or when $R_3$ and $R_4$ are attached to a single nitrogen atom, they can be taken together as

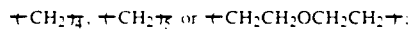

J and K are independently selected from a 5- or 6-membered heteroaromatic rings independently containing 1 or 2 heteroatoms independently selected from 0 to 1 oxygen, 0 to 1 sulfur and 0 to 2 nitrogen atoms, attached via carbon and optionally substituted by one or more substituents independently selected from W;

X' is

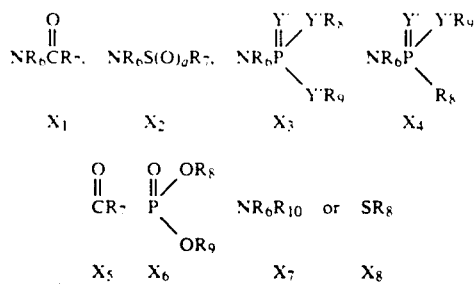

$R_6$ and $R_{10}$ are independently selected from $C_1$ to $C_6$ alkyl, $C_1$-$C_6$ haloalkyl, $C_3$-$C_6$ cycloalkyl, $C_4$-$C_7$ cycloalkylalkyl, $C_2$ to $C_6$ cyanoalkyl, $C_2$ to $C_6$ alkoxyalkyl, $C_3$ to $C_8$ alkoxycarbonylalkyl, $C_4$ to $C_8$ dialkylaminocarbonylalkyl, phenyl optionally substituted by 1 to 2 substituents selected from W, benzyl optionally substituted by 1 to 2 substituents selected from W, and phenethyl optionally substituted by 1 to 2 substituents selected from W, or $R_6$ and $R_{10}$ can be taken together as $(CH_2)_4$, $(CH_2)_5$ or $(CH_2)_2O(CH_2)_2$, each ring being optionally substituted with 1 to 2 $CH_3$;

$R_7$ is F, $C_1$-$C_{20}$ alkyl, $C_1$-$C_6$ haloalkyl, $C_2$-$C_8$ dialkylamino,

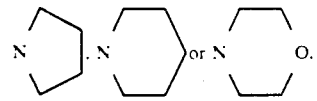

each ring being optionally substituted with 1 to 2 $CH_3$; phenyl optionally substituted by 1 to 2 substituents selected from W, or $R_7$ is $C_1$-$C_{20}$ alkoxy, $C_1$-$C_4$ alkoxy substituted by cyano, nitro, $C_1$-$C_4$ alkoxy, $C_4$-$C_8$ alkoxyalkoxy, $C_1$-$C_2$ alkylthio, $C_2$-$C_3$ alkoxycarbonyl, $C_3$-$C_5$ dialkylaminocarbonyl, phenyl or 1 to 6 halogens, or $R_7$ is phenoxy optionally substituted by 1 to 2 substituents selected from W, $R_8$ and $R_9$ are independently selected from $C_1$-$C_4$ alkyl, $C_2$-$C_4$ haloalkyl or phenyl optionally substituted by 1 to 2 substituents selected from W or $R_8$ and $R_9$ may be taken together as $(CH_2)_2$, $(CH_2)_3$ or $CH_2C(CH_3)_2CH_2$;

a is 0 to 2;

Y' is O or S;

m is 1 to 3;

n is 0 to 3; and p is 0 to 3;

provided that R is K when A is not J.

In the above definitions, the term "alkyl", used either alone or in compound words such as "alkylthio" or "haloalkyl", includes straight chain or branched alkyl, e.g., methyl, ethyl, n-propyl, isopropyl or the different butyl, pentyl, hexyl isomers.

Alkoxy includes methoxy, ethoxy, n-propyloxy, isopropyloxy and the different butoxy or pentoxy isomers.

Alkenyl includes straight chain or branched alkenes, e.g., vinyl, 1-propenyl, 2-propenyl, 3-propenyl and the different butenyl, pentenyl and hexenyl isomers.

Alkynyl includes straight chain or branched alkynes, e.g., ethynyl, 1-propynyl, 2-propynyl and the different butynyl, pentynyl and hexynyl isomers.

Alkylthio includes methylthio, ethylthio and the different propylthio and butylthio isomers.

Alkylsulfinyl, alkylsulfonyl, alkylamino, etc., are used analogously to the above examples.

Cycloalkyl includes cyclopropyl, cyclobutyl, cyclopentyl and cyclohexyl.

The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_2$ and $CH_2CHFCl$. The terms "halocycloalkyl", "haloalkenyl" and "haloalkynyl" are used analogously to "haloalkyl". The term "compound(s)" employed herein includes all isomers and agriculturally suitable salts thereof.

The total number of carbon atoms in a substituent group is indicated by the "$C_i$ to $C_j$" prefix where i and j are numbers from 1 to 8. For example, $C_1$ to $C_3$ alkylsulfonyl would designate methylsulfonyl through propylsulfonyl; $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl would designate $CH_2CN$ and $C_3$ cyanoalkyl would designate $CH_2CH_2CN$ and $CH(CN)CH_3$; $C_2$ alkylcarbonyl would designate C(O)CH₃ and C₄ alkylcarbonyl would include C(O)CH₂CH₂CH₃ and C(O)CH(CH₃)₂; and as a final example, C₃ alkoxycarbonylalkyl would designate CH₂CO₂CH₃ and C₄ alkoxycarbonylalkyl would include CH₂CH₂CO₂CH₃, CH₂CO₂CH₂CH₃ and CH(CH₃)CO₂CH₃.

Preferred for higher insecticidal activity are compounds (Group A) of Formula I wherein R is

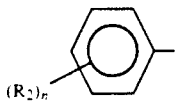

and

A is J.

Also preferred are the compounds (Group B) of preferred Group A wherein:

X is O;
Y is H, CH₃, SCH₃, SSCl₃, SC₆H₅, 2-(NO₂)C₆H₄S, C(O)CH₃, C(O)H, C(O)CF₃, CO₂CH₃, CO₂CH₃, CO₂C₂H₅ or SX';
X' is X₁, X₂, X₃, X₄, X₅ or X₇;
R₆ and R₁₀ are independently selected from C₁-C₆ alkyl, C₁-C₆ haloalkyl, C₅-C₆ cycloalkyl, C₃-C₈ alkoxycarbonylalkyl, phenyl, benzyl or phenethyl each optionally substituted with W or R₆ and R₁₀ may be taken together as (CH₂)₄, (CH₂)₅ or (CH₂)₂O(CH₂)₂;
R₈ and R₉ are independently selected from C₁-C₃ alkyl and phenyl;
a is 2;
R₃ is C₁ to C₄ alkyl, C₁ to C₂ haloalkyl, C₂ to C₄ alkenyl, C₂ to C₄ haloalkenyl, propargyl, phenyl, benzyl; or phenyl or benzyl substituted with one of F, Cl, Br, CF₃, OCF₂H, OCF₃ or NO₂;
B is H, C₁ to C₆ alkyl, C₁ to C₆ haloalkyl, C₂ to C₆ alkoxyalkyl, C₂ to C₆ cyanoalkyl, C₃ to C₈ alkoxycarbonylalkyl, C₁ to C₆ alkenyl, C₁ to C₆ alkynyl or C₂ to C₆ alkoxycarbonyl;
n is 0 to 2; and
m is 1 to 2.

Also preferred are the compounds (Group C) of preferred Group B wherein:

R₁ is halogen, CN, SCN, NO₂, R₃, OR₃, SR₃, S(O)₂R₃, CO₂R₃ or C(O)R₃, or when m is 2, R₁ can be taken together as —OCH₂CH₂O—, —CH₂C(CH₃)₂O—, —OCF₂CF₂O— or —CF₂CF₂O—;
R₂ is halogen, CN, SCN, NO₂, R₃, OR₃, SR₃, S(O)₂R₃, OC(O)R₃, OS(O)₂R₃, CO₂R₃, C(O)R₃, C(O)NR₃R₄, S(O)₂NR₃R₄ or NR₃R₄;
R₃ is C₁ to C₄ alkyl, C₁ to C₂ haloalkyl, C₂ to C₄ alkenyl, C₂ to C₄ haloalkenyl or propargyl;
R₄ is H or C₁ to C₂ alkyl;
W is halogen, CN, CO₂CH₃, C(O)NHCH₃, C(O)N(CH₃)₂, NO₂, CH₃, CF₃, OCH₃, OCF₂H, OCF₂CF₂H, SCH₃, SCF₂H, SCF₂CF₂H or S(O)₂CH₃;
B is H, C₁ to C₄ alkyl, C₁ to C₄ haloalkyl, or C₃ to C₄ alkenyl;
J is

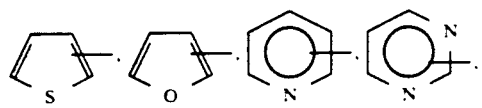

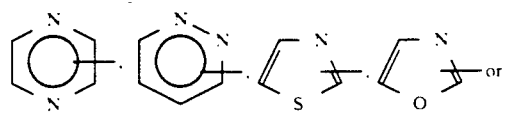

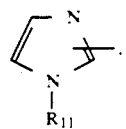

optionally substituted by one substituent selected from W; and
R₁₁ is H or C₁ to C₂ alkyl.

Also preferred are the compounds (Group D) of preferred Group C wherein:
Y is H, CH₃, C(O)CH₃, CO₂CH₃ or SX';
X' is X₁, X₂, X₃ or X₅;
R₆ is C₁-C₄ alkyl, CF₃, cyclohexyl, phenyl optionally substituted by W, or benzyl optionally substituted by W;
R₇ is F, C₁-C₁₂ alkyl, C₁-C₆ haloalkyl, phenyl or phenoxy each optionally substituted by W, C₁-C₁₂ alkoxy, dimethylamino or C₁-C₄ alkoxy substituted with NO₂, C₂-C₄ alkoxy or 1-6 halogens;
m is 1 or 2 and one substituent is in the 4-position of the phenyl ring;
n is 0, 1 or 2 and one substituent is in the 4-position of the phenyl ring;
R₁ is F, Cl, Br, CF₃, OCF₂H, OCF₃, CN, or when m is 2, R₁ can be taken together as —CH₂C(CH₃)₂O— or —CF₂CF₂O—;
R₂ is F, Cl, Br, CN, NO₂, CF₃, CH₃, OCH₃, OCF₂H, OCF₃, SCH₃, SCF₂H, S(O)₂CH₃ or N(CH₃)₂; and
B is H or CH₃.

Also preferred are the compounds (Group E) of Formula I wherein:
R is K and
A is C₁ to C₆ alkyl, phenyl, phenyl substituted by (R₅)ₚ, CO₂R₃, C(O)R₃, C(O)NR₃R₄, C(S)NR₃R₄, C(S)R₃ or C(S)SR₃.

Also preferred are the compounds (Group F) of Group E wherein:
X is O;
Y is H, CH₃, SCH₃, SCCl₃, SC₆H₅, 2-(NO₂)C₆H₄S, C(O)CH₃, C(O)H, C(O)CF₃, CO₂CH₃, CO₂C₂H₅ or SX';
X' is X₁, X₂, X₃, X₄, X₅ or X₇;
R₆ and R₁₀ are independently selected from C₁-C₆ alkyl, C₁-C₆ haloalkyl, C₅-C₆ cycloalkyl, C₃-C₈ alkoxycarbonylalkyl, phenyl, benzyl or phenethyl each optionally substituted with W or R₆ and R₁₀ may be taken together as (CH₂)₄, (CH₂)₅ or (CH₂)₂O(CH₂)₂;
R₈ and R₉ are independently selected from C₁-C₃ alkyl and phenyl;
a is 2;
R₃ is C₁ to C₄ alkyl, C₁ to C₂ haloalkyl, C₂ to C₄ alkenyl, C₂ to C₄ haloalkenyl, propargyl, phenyl, benzyl, or phenyl or benzyl each substituted with one of F, Cl, Br, CF₃, OCF₂H, OCF₃ or NO₂;
m is 1 to 2; and
p is 0 to 2.

Also preferred are the compounds (Group G) of Group F wherein:
R₁ is halogen, CN, SCN, NO₂, R₃, OR₃, SR₃, S(O)₂R₃, CO₂R₃ or C(O)R₃, or when m is 2, R₁ can be taken together as —OCH$_2$CH$_2$O—, —CH$_2$C(CH$_3$)$_2$O—, —OCF$_2$CF$_2$O— or —CF$_2$CF$_2$O—;

R$_3$ is C$_1$ to C$_4$ alkyl, C$_1$ to C$_2$ haloalkyl, C$_2$ to C$_4$ alkenyl, C$_2$ to C$_4$ haloalkenyl or propargyl;

R$_4$ is H or C$_1$ to C$_2$ alkyl;

R$_5$ is halogen, CN, SCN, NO$_2$, R$_3$, OR$_3$, SR$_3$, S(O)$_2$R$_3$, OC(O)R$_3$, OS(O)$_2$R$_3$, CO$_2$R$_3$, C(O)R$_3$, C(O)NR$_3$R$_4$, S(O)$_2$NR$_3$R$_4$ or NR$_3$R$_4$;

W is halogen, CN, CO$_2$CH$_3$, C(O)NHCH$_3$, C(O)N(CH$_3$)$_2$, NO$_2$, CH$_3$, CF$_3$, OCH$_3$, OCF$_2$H, OCF$_2$CF$_2$H, SCH$_3$, SCF$_2$H, SCF$_2$CF$_2$H or S(O)$_2$CH$_3$;

A is C$_1$ to C$_4$ alkyl, phenyl, phenyl substituted with (R$_5$)$_p$, CO$_2$R$_3$, C(O)R$_3$, C(O)NR$_3$R$_4$ or C(O)N(R$_4$)-phenyl said phenyl optionally substituted with F, Cl, Br, CF$_3$, OCF$_2$H, OCF$_3$ or NO$_2$;

B is H, C$_1$ to C$_4$ alkyl, C$_1$ to C$_4$ haloalkyl, or C$_3$ to C$_4$ alkenyl; and K is

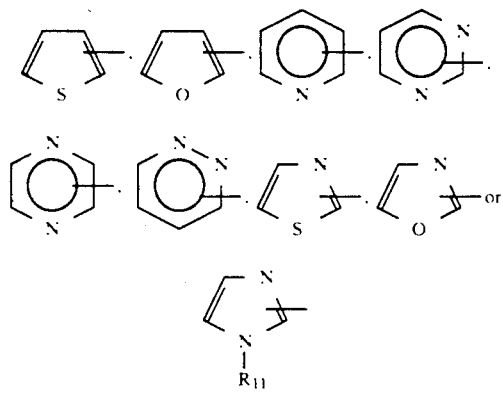

substituted by at least one substituent selected from W; and

R$_{11}$ is H or C$_1$ to C$_2$ alkyl.

Also preferred are the compounds (Group H) of Group G wherein:

Y is H, CH$_3$, C(O)CH$_3$, CO$_2$CH$_3$ or SX';

X' is X$_1$, X$_2$, X$_3$ or X$_5$;

R$_6$ is C$_1$-C$_4$ alkyl, CF$_3$, cyclohexyl, phenyl optionally substituted by W, or benzyl optionally substituted by W;

R$_7$ is F, C$_1$-C$_{12}$ alkyl, C$_1$-C$_6$ haloalkyl, phenyl or phenoxy optionally substituted by W, C$_1$-C$_{12}$ alkoxy, dimethylamino or C$_1$-C$_4$ alkoxy substituted with NO$_2$, C$_2$-C$_4$ alkoxy or 1-6 halogens;

R$_1$ is F, Cl, Br, CF$_3$, OCF$_2$H, OCF$_3$, CN, or when m is 2, R$_1$ can be taken together as —CH$_2$C(CH$_3$)$_2$O— or —CF$_2$CF$_2$O—;

R$_5$ is F, Cl, Br, CN, NO$_2$, CF$_3$, CH$_3$, OCH$_3$, OCF$_2$H, OCF$_3$, SCH$_3$, SCF$_2$H, S(O)$_2$CH$_3$, S(O)$_2$CF$_2$H, CO$_2$CH$_3$, C(O)NHCH$_3$, C(O)N(CH$_3$)$_2$, S(O)$_2$N(CH$_3$)$_2$ or N(CH$_3$)$_2$;

A is phenyl or phenyl substituted with (R$_5$)$_p$;

B is H or CH$_3$;

m is 1 or 2 and one substituent is in the 4-position of the phenyl ring; and p is 0, 1 or 2 and one substituent is in the 3 or 4-position of the phenyl ring.

Also preferred are the compounds (Group I) of Group G wherein:

Y is H, CH$_3$, C(O)CH$_3$ or CO$_2$CH$_3$;

X' is X$_1$, X$_2$ or X$_5$;

R$_6$ is C$_1$-C$_4$ alkyl or phenyl optionally substituted with CH$_3$ or Cl;

R$_7$ is C$_1$-C$_6$ alkyl, C$_1$-C$_6$ haloalkyl, C$_1$-C$_{12}$ alkoxy, dimethylamino or phenyl optionally substituted with CH$_3$ or Cl;

R$_1$ is F, Cl, Br, CF$_3$, OCF$_2$H, OCF$_3$ or CN;

A is CO$_2$CH$_3$, CO$_2$C$_2$H$_5$, C(O)NHCH$_3$ or C(O)N(CH$_3$)$_2$;

B is CH$_3$; and m is 1 or 2 and one substituent is in the 4-position of the phenyl ring.

Specifically preferred compounds are:

1-(4-chlorophenyl)-5-(2-furanyl)-4,5-dihydro-N-[4-(trifluoromethyl)phenyl]-1H-pyrazole-3-carboxamide, 1-(5-chloro-2-pyridinyl)-5-(4-fluorophenyl)-4,5-dihydro-N-[4-(trifluoromethyl)phenyl]-1H-pyrazole-3-carboxamide, 1-(5-bromo-2-pyridinyl)-5-(4-fluorophenyl)-4,5-dihydro-N-[4-(trifluoromethyl)phenyl]-1H-pyrazole-3-carboxamide, 1-(4-chlorophenyl)-5-(5-chloro-2-pyridinyl)-4,5-dihydro-5-methyl-N-[4-(trifluoromethyl)phenyl]-1H-pyrazole-3-carboxamide, and 1-(4-chlorophenyl)-5-(5-chloro-2-thienyl)-4,5-dihydro-N-[4-(trifluoromethyl)phenyl]-1H-pyrazole-3-carboxamide.

DETAILS OF THE INVENTION

Compounds of Formula I can be obtained by the reaction of activated carbonyl or thiocarbonyl compounds of Formula II with substituted anilines in the presence or absence of an acid acceptor or suitable condensing agent. Methods for performing this transformation are well known in the art; see, Zabicky, "The Chemistry of the Amides", Interscience, 1970.

One particularly useful method involves the chlorination of an acid derivative (II, X$_1$=OH) with thionyl chloride or another chlorinating agent followed by treatment with an aniline (III) in the presence of an acid acceptor such as an amine base, preferably triethylamine. Suitable solvents for the chlorination reaction are inert to hydrogen chloride and include benzene, toluene, and dichloromethane. Preferred temperatures for this process are from 20° to 100° C. with temperatures between 20° and 80° C. being particularly preferred. The latter reaction can be carried out in many different inert solvents such as dialkylethers, chlorinated hydrocarbons, and aromatic hydrocarbons. While temperatures at or below 25° C. are preferred, higher temperatures can also be employed. These reactions are normally run at atmospheric pressure, but can also be carried out at elevated pressures.

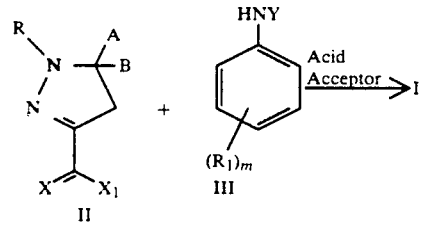

Esters of Formula II (X$_1$=C$_1$ to C$_6$ alkoxy) can be converted directly to compounds of Formula I in several ways. In the presence of Lewis acids such as AlMe$_3$, anilines react readily with esters of Formula II. The reaction is best carried out at room temperature to 120° C. Suitable solvents include dichloromethane, 1,2-dichloroethane, and toluene. The method described by Weinreb et al., *Organic Synthesis*, 59, 49, (1982), proceeds best with esters of lower alcohols such as methanol or ethanol.

Acids of Formula II ($X_1$=OH) can be converted directly to compounds of Formula I by use of coupling agents known in the peptide art in conjunction with anilines. Coupling agents include dicyclohexylcarbodiimide (DCC), N-hydroxysuccinimide, 2-chloro-N-methylpyridinium iodide, carbonyl diimidazole, or other agents capable of activating an acid function or acting as a dehydrating agent. These and other methods are described in Gross et al., "The Peptides," 3 Vols., Academic Press, New York, 1979 to 1981.

Compounds of Formula I can also be obtained from the cyclization of appropriate phenyl or heteroaryl hydrazines (V) with keto-acid derivatives (IV). It will be appreciated by those skilled in the art that this process applies equally to acids, esters, and anilides and further that the interconversion of these groups as discussed in the sequence (II→I) can be carried out after the cyclization reaction. The conditions for these reactions are well known in the art and described by Hill et al., *Trans. Illinois Acad. Sci.*, 33 (1940), 112 and by Vaughan, *J. Org. Chem.*, 20 (1955), 1619. The cyclization reaction is best carried out on an unsaturated keto-acid derivative (IV) in refluxing alcoholic media, in refluxing lower carboxylic acids, or in polar aprotic solvents such as dimethylformamide or dimethyl sulfoxide. Ethanol containing acetic acid or acetic acid alone are the preferred solvents although other protic or aprotic solvents and mixtures are also applicable. In some cases, phenyl hydrazones can be isolated prior to final cyclization and these can be refluxed further in order to complete the cyclization. While the unsaturated acid derivatives (IV) are preferred, saturated compounds with a reactive group such as a halogen beta to the carbonyl can be employed in certain instances. The most Preferred Z substituents for the cyclization are the acids and anilides.

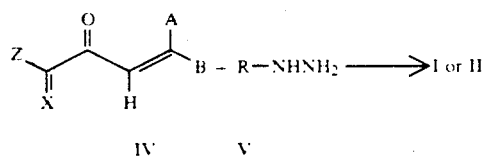

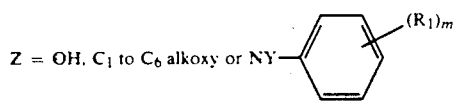

Many of the required aryl and heteroaryl hydrazines (V) are available from commercial sources. The synthesis of these substrates is well known in the art; see Enders in Houben-Weyl's "Methoden der Organischen Chemie", Vol. 10/2; 177 to 348, Georg Thieme Verlag, Stuttgart, 1967.

Compounds of Formula I and intermediates of Formula II can also be obtained by the dipolar cycloaddition reaction of nitrile-imines, generated from substituted phenylhydrazones of Formula VI, with appropriately substituted alkenes. The presence of an acid acceptor (generally an amine base, for example, triethylamine) is necessary for the formation of the nitrile-imine. In a typical reaction, the alkene is used in a two- to five-fold molar excess and the amine base in a three- to five-fold excess based on the hydrazone (VI). Suitable solvents include but are not restricted to benzene, toluene, 1,2-dichloroethane, chloroform, and tetrahydrofuran. The reaction can be carried out at temperatures ranging from 20° to 120° C. with the relative reactivity of the alkene (VII) governing the required temperature for a given example. The required hydrazones (VI) for the synthesis of compounds of Formula I and II can be prepared by methods known in the art or by modifications thereof; see, e.g., Shawali et al., *Tetrahedron*, 20 (1971), 2517.

The alkenes such as (VII) used in cycloaddition reactions are generally available commercially. Other alkenes can be synthesized by many methods such as those described in March, "Advanced Organic Chemistry", 3rd Edition. Wiley, New York, pages 1149 to 1151.

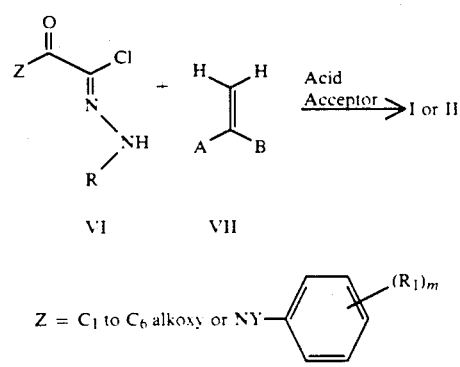

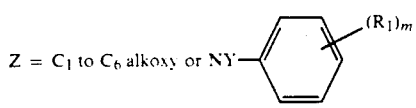

Nitrile-imines may also be generated by other methods which may be better suited for basic nitrogen containing heterocycles such as pyridine. The thermal or photolytic decomposition of 2,5-disubstituted tetrazoles produces nitrile-imines. Tetrazoles (VIII) suitable for use in the present invention may be obtained by the general route of Lippmann et al. (*Monatshefte für Chemie*, 106, 1975, 437.). The thermolysis of tetrazoles generally requires high temperatures from 200° to 400° C. Photolysis with high intensity lamps can be performed on these compounds at room temperature to 120° C. Suitable solvents include benzene, dioxane, and toluene. The reaction is best performed in dilute solutions in the presence of one or more equivalents of an alkene. Use of $CuSO_4$ solution or a pyrex filter in the photolysis apparatus is preferred.

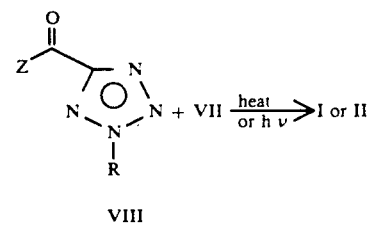

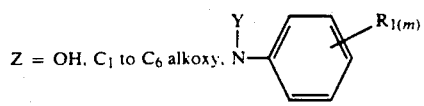

The photolysis of syndnones is another method of nitrile-imine generation. Irradiation of a dilute solution of the sydnone (IX) (about 0.05M) in the presence of an excess of the alkene at or near room temperature gives the compounds of the present invention. Sydnones (IX) of the desired structures can be obtained by the metallation of the sydnones (X) and subsequent reaction with phenylisocyanates, chloroformates, or carbon dioxide. Metallation and trapping of the sydnones is best performed at temperatures lower than −20° C. Typical solvents used are diethyl ether and tetrahydrofuran. Metallation can be accomplished with n-butyl lithium and other alkyl lithium bases.

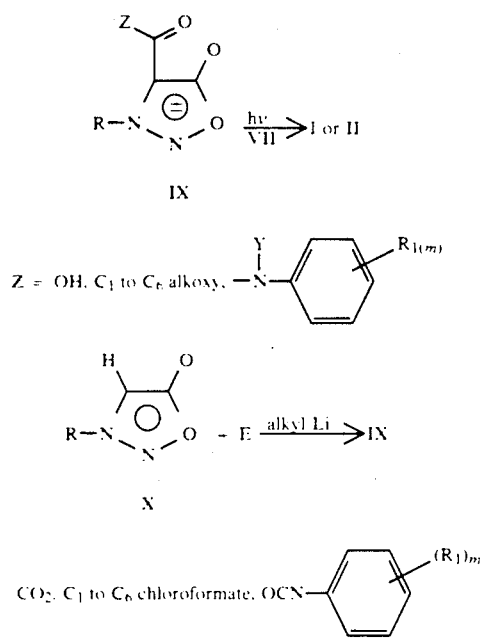

Certain reactions can be used to convert various functional groups into heterocycles on already formed pyrazolines (I or II). One convenient method involves taking an aldehyde (I or II A=CHO) and treating it with p-toluene sulfonyl isocyanide (TOSMIC) and an acid acceptor. The resulting product is an oxazole (I or II A=oxazole). The reaction is carried out in polar organic solvents such as alcohols. The preferred bases are inorganic salts such as potassium carbonate, sodium carbonate or potassium bicarbonate.

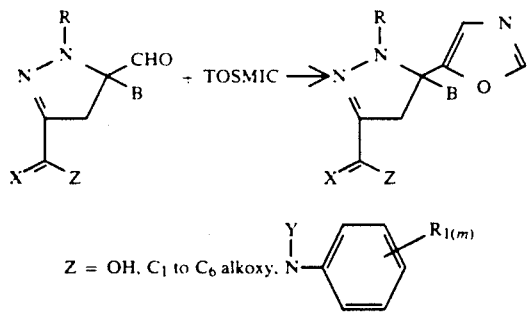

Some compounds of Formula I (Y=H) can be converted to other compounds of Formula I by alkylation, acylation, and sulphenylation reactions (Y=H). Reaction of compounds of Formula I in the presence of an acid acceptor with electrophilic agents (Y=leaving group) results in substitution on nitrogen. Strong bases such as sodium hydride, potassium t-butoxide, potassium hydride, and other bases known in the art to deprotonate amides are preferred in the process. Suitable electrophiles include, but are not restricted to alkyl halides, acyl halides, acid anhydrides, carbonates, chloroformates, disulphides, and sulphenyl halides. This reaction is normally run in the temperature range of 0° to 25° C., but can be run at temperatures up to 120° C. if unreactive electrophiles are used. Solvents not deprotonated under the reactions conditions such as tetrahydrofuran, dimethylformamide, dimethoxyethane, and diethyl ether are preferred.

Compounds of Formula I (X=O) can be converted to compounds of Formula I (X=S) by means of thiating agents. Conversion of amides to thioamides is well known in the art. Phosphorous pentasulfide either alone or in combination with organic or inorganic bases is a preferred reagent to effect this conversion. When phosphorous pentasulfide is used alone, organic bases such as pyridine are the preferred solvents. When it is used in conjunction with inorganic bases such as sodium bicarbonate, the preferred solvents are ethers such as diglyme. Temperatures between 20° to 160° C. can be employed successfully with temperatures between 90° to 120° C. preferred. These and other means to convert amides to thioamides are described by Lapucha, *Synthesis* (1987), 256.

It will be appreciated by those skilled in the art that, regardless of the method of synthesis, compounds of Formula II can be converted to compounds of the instant invention by the methods described above. Many functional group transformations known to those skilled in the art can be employed to convert compounds of Formula I to new compounds of Formula I and that this will overcome any incompatibility of certain such groups with reagents and conditions disclosed above with respect to typical reaction mechanisms.

The following examples illustrate the invention.

EXAMPLE 1

Methyl chloro[2-(4-chlorophenyl)hydrazono]acetate

To a suspension of 4-chloroaniline (41.75 g) in 6N HCl (170 ml) cooled to 0° C. was slowly added a solution of sodium nitrite (23.9 g) in water. The resulting cold solution was added gradually by means of an insulated dropping funnel to a suspension of 2-chloroacetoacetate (40 ml) and sodium acetate (85.2 g) in ethanol (450 ml). The reaction mixture was vigorously stirred and cooled to keep the temperature below 10° C. during the addition. The reaction was then allowed to warm to room temperature. The precipitated product was filtered, washed with water and air dried. Recrystallization from benzene gave the product in 2 crops (56.0 g). m.p.: 149° to 150° C., NMR (CDCl$_3$); 8.3 (m, HH); 7.3 (m, 2H); 7.1 (m, 2H); 3.9 (s, 3H, CH$_3$).

EXAMPLE 2

Methyl 1-(4-chlorophenyl)-5-(2-furanyl)-4,5-dihydro-1H-pyrazole-3-carboxylate

The compound of Example 1 (2.0 g) was suspended in benzene (20 ml) and heated to reflux in the presence of 2-vinylfuran (2.5 ml). Triethylamine was added and the mixture was allowed to reflux for 1 hour longer. The mixture was partitioned between water and ethyl acetate. The ethyl acetate layer was dried over magnesium sulfate and concentrated. Chromatography on silica gel (5:1 hexanes/ethyl acetate) gave the title compound (1.8 g). NMR (CDCl₃) 7.3 to 6.9 (m, Ar-H, 5H); 6.2 (m, Furan-H, 2H); 5.5 (dd, CH, 1H); 3.9 (s, OCH₃, 3H); 3.6 (m, CH, 1H); 3.4 (m, CH₂, 1H).

EXAMPLE 3

1-(4-Chlorophenyl)-5-(2-furanyl)-4,5-dihydro-N-[4-(trifluoromethyl)phenyl]-1H-pyrazole-3-carboxamide The compound of Example 2 (1.4 g) was heated to reflux in methanol (20 ml) with 50% sodium hydroxide (1.0 ml) for 1 hour. The mixture was cooled and acidified with 1N HCl. Extraction with ethyl acetate, drying, and evaporation gave the acid. The acid was suspended in benzene (10 ml) and heated to reflux with thionyl chloride (1.5 ml). After heating for 2 hours, the mixture was evaporated and azeotroped with toluene (10 ml). The residue was dissolved in tetrahydrofuran (20 ml) and divided in two. One aliquot was added to a stirred mixture of 4-amino benzotrifluoride (0.3 ml) and triethylamine (0.5 ml). After 30 minutes of stirring, the mixture was diluted with 1N HCl (50 ml) and ethyl acetate (50 ml). The ethyl acetate layer was washed with sodium bicarbonate solution (50 ml) and with brine (50 ml). Drying over magnesium sulfate and evaporation provided the crude product. Recrystallization from methylene chloride/methanol gave the title compound (0.54 g). m.p.: 167° to 171° C. NMR (CDCl₃) 8.6 (Br, NH); 7.7-7.1 (m, ArH, 9H); 6.3 (m, furan-H, 2H); 5.5 (m, CH, 1H); 3.7 (m, CH, 1H); 3.5 (m, CH, 1H).

EXAMPLE 4

1-(6-Chloro-3-pyridazinyl)-5-(4-fluorophenyl)-4,5-dihydro-N-[4-(trifluoromethyl)phenyl]-1H-pyrazole-3-carboxamide Part A: To make potassium 4-(4-fluorophenyl)-2-oxo-3-butenoate, a solution of pyruvic acid and p-fluorobenzaldehyde (24.8 g) in methanol (20 ml) were cooled to 15° C. and treated with a solution of potassium hydroxide (16.8 g) in (50 ml) methanol. After ⅔ of the addition was complete, the cooling bath was removed and the temperature was allowed to rise to 40° C. A yellow precipitate appeared and was filtered after standing overnight. The solid was washed well with methanol and ether. The compound (34.5 g) was used without further purification in Part B.

Part B: The compound of Part A was converted to the corresponding carboxylic acid by the general method of Stecher (J. Am. Chem. Soc., 1952, 74, 4392). The free acid (from 8 g of potassium salt) was suspended in benzene (150 ml) and thionyl chloride (6 ml). The mixture was heated to reflux for 10 minutes with dimethylformamide (4 drops) and allowed to cool to room temperature. After stirring for 4 hours the mixture was concentrated under reduced pressure. The residue was dissolved in tetrahydrofuran (100 ml) and then added dropwise with cooling to a solution of triethylamine (10 ml) and 4-aminobenzotrifluoride (6.5 g). The mixture was stirred for 30 minutes and partitioned between ethyl acetate and 1N HCl. The organic layer was washed with saturated sodium bicarbonate, dried, and evaporated. The solid residue was recrystallized from butyl chloride to give 4-(4-fluorophenyl)-2-oxo-N-[4-(trifluoromethyl)phenyl]-3-butenamide (5.2 g) m.p.: 200° to 201° C.; NMR (CDCl₃); 9.2 (Br, NH); 8.0 to 7.1 (m, Ar and CH₂, 10H).

Part C: The compound of Part B (0.9 g) was dissolved in dimethylformamide (8 ml) and treated with 6-chloro-3-hydrazinopyridazine (0.3 g) and then heated for 2 hours at reflux. The solvent was evaporated under reduced pressure. The residue was chromatographed on silica gel (hexane/ethyl acetate (3:1)). The main fraction was crystallized by addition of hexane to give the title compound (0.53 g). m.p.: 200° to 202° C.; NMR (CDCl₃): 8.6 (br, NH); 7.8 to 6.9 (m, ArH, 10H); 5.9 (dd, CH, 1H); 3.85 (dd, 1H, CH); 3.3 (dd, CH, 1H).

EXAMPLE 5

1-(5-Chloro-2-pyridinyl)-5-(4-fluorophenyl)-4,5-dihydro-N-(4-trifluoromethyl)phenyl-1H-pyrazole-3-carboxamide The procedure for Example 4 was used and 5-chloro-2-pyridyl hydrazine (0.34 g) was substituted in Part C to yield the title compound (0.49 g). m.p.: 175 to 177 (MeOH); NMR (CDCl₃): 8.6 (NH), 8.0 to 7.0 (m, ArH); 5.8 (m, CH); 3.8 (m, CH); 3.2 (m, CH).

EXAMPLE 6

1H-Pyrazole-3-carboxamide, 1-(4-fluorophenyl)-4,5-dihydro-5-methyl-5-(5-oxazolyl)-N-((4-trifluoromethyl)phenyl))

The starting material, 1H-pyrazole-3-carboxamide, 1-(4-fluorophenyl)-5-formyl-4,5-dihydro-5-methyl-N-((4-(trifluoromethyl)phenyl)), was synthesized by the general procedures for Examples 1 to 3 using p-fluoroaniline instead of p-chloroaniline in Example 1 and methacrolein in place of 2-vinylfuran in Example 2. The starting material (0.5 g) and p-toluenesulfonylisocyanide (0.24 g) were suspended in methanol (5 ml) and stirred at room temperature for 4 hours. The mixture was poured into water (100 ml) and extracted with ethyl acetate (3×100 ml). The organic layer was dried and evaporated. The residue was chromatographed on silica gel (hexanes/ethyl acetate 1:1) to give the title compound as a solid (0.27 g); m.p.=142° to 145° C. NMR (CDCl₃) 8.2-6.9 (m, ArH and NH, 10H); 3.6 (m, 2H, CH₂); 1.69 (s, CH₃, 3H).

Generic structures for the compound species listed in Tables 1 to 5 are as follows:

TABLE 1

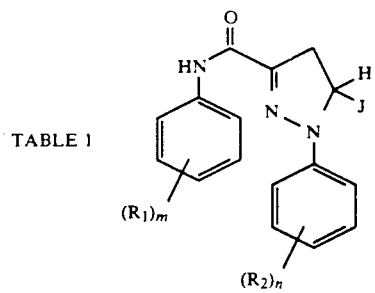

TABLE 2

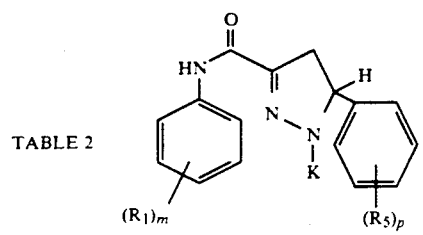

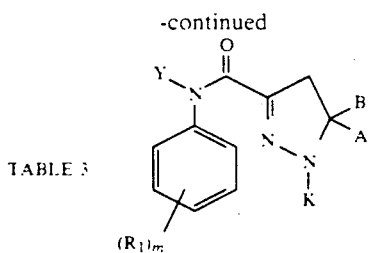

TABLE 3

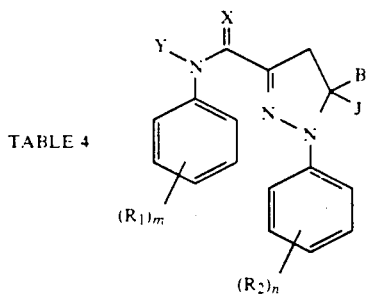

TABLE 4

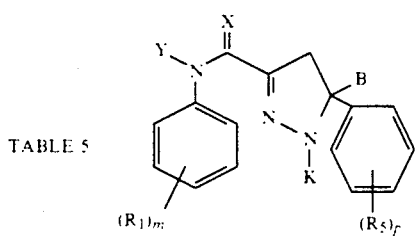

TABLE 5

TABLE 1

| R₁ | R₂ | J | (m.p. °C) |
|---|---|---|---|
| 4-CF₃ | 4-Cl | 2-pyridyl | 174 to 174.5 |
| 4-CF₃ | 4-F | 2-pyridyl | |
| 4-CF₃ | 4-OCF₂H | 2-pyridyl | |
| 4-CF₃ | 4-CF₃ | 2-pyridyl | |
| 4-CF₃ | 4-CN | 2-pyridyl | |
| 4-CF₃ | 4-OCF₃ | 2-pyridyl | |
| 4-CF₃ | 4-Cl | 3-pyridyl | |
| 4-CF₃ | 4-F | 3-pyridyl | |
| 4-CF₃ | 4-OCF₂H | 3-pyridyl | |
| 4-CF₃ | 4-CF₃ | 3-pyridyl | |
| 4-CF₃ | 4-CN | 3-pyridyl | |
| 4-CF₃ | 4-OCF₃ | 3-pyridyl | |
| 4-CF₃ | 4-Cl | 4-pyridyl | |
| 4-CF₃ | 4-F | 4-pyridyl | |
| 4-CF₃ | 4-OCF₂H | 4-pyridyl | |
| 4-CF₃ | 4-CF₃ | 4-pyridyl | |
| 4-CF₃ | 4-CN | 4-pyridyl | |
| 4-CF₃ | 4-OCF₃ | 4-pyridyl | |
| 4-CF₃ | 4-Cl | 5-Cl-pyrid-2-yl | 175 to 177 |
| 4-CF₃ | 4-F | 5-Cl-pyrid-2-yl | |
| 4-CF₃ | 4-OCF₂H | 5-Cl-pyrid-2-yl | |
| 4-CF₃ | 4-CF₃ | 5-Cl-pyrid-2-yl | |
| 4-CF₃ | 4-CN | 5-Cl-pyrid-2-yl | |
| 4-CF₃ | 4-OCF₃ | 5-Cl-pyrid-2-yl | |
| 4-CF₃ | 4-Cl | 6-Cl-pyrid-3-yl | |
| 4-CF₃ | 4-F | 6-Cl-pyrid-3-yl | |
| 4-CF₃ | 4-OCF₂H | 6-Cl-pyrid-3-yl | |
| 4-CF₃ | 4-CF₃ | 6-Cl-pyrid-3-yl | |
| 4-CF₃ | 4-CN | 6-Cl-pyrid-3-yl | |
| 4-CF₃ | 4-OCF₃ | 6-Cl-pyrid-3-yl | |
| 4-CF₃ | 4-Cl | 6-F-pyrid-3-yl | |
| 4-CF₃ | 4-F | 6-F-pyrid-3-yl | |
| 4-CF₃ | 4-OCF₂H | 6-F-pyrid-3-yl | |
| 4-CF₃ | 4-CF₃ | 6-F-pyrid-3-yl | |
| 4-CF₃ | 4-CN | 6-F-pyrid-3-yl | |
| 4-CF₃ | 4-OCF₃ | 6-F-pyrid-3-yl | |
| 4-CF₃ | 4-Cl | 2-thienyl | |
| 4-CF₃ | 4-F | 2-thienyl | |
| 4-CF₃ | 4-OCF₂H | 2-thienyl | |
| 4-CF₃ | 4-CF₃ | 2-thienyl | |
| 4-CF₃ | 4-CN | 2-thienyl | |

TABLE 1-continued

| R₁ | R₂ | J | (m.p. °C) |
|---|---|---|---|
| 4-CF₃ | 4-OCF₃ | 2-thienyl | |
| 4-CF₃ | 4-Cl | 3-thienyl | 204 to 206 |
| 4-CF₃ | 4-F | 3-thienyl | |
| 4-CF₃ | 4-OCF₂H | 3-thienyl | |
| 4-CF₃ | 4-CF₃ | 3-thienyl | |
| 4-CF₃ | 4-CN | 3-thienyl | |
| 4-CF₃ | 4-OCF₃ | 3-thienyl | |
| 4-CF₃ | 4-Cl | 5-Cl-thien-2-yl | |
| 4-CF₃ | 4-F | 5-Cl-thien-2-yl | |
| 4-CF₃ | 4-OCF₂H | 5-Cl-thien-2-yl | |
| 4-CF₃ | 4-CF₃ | 5-Cl-thien-2-yl | |
| 4-CF₃ | 4-CN | 5-Cl-thien-2-yl | |
| 4-CF₃ | 4-OCF₃ | 5-Cl-thien-2-yl | |
| 4-CF₃ | 4-Cl | 5-Cl-thien-3-yl | |
| 4-CF₃ | 4-F | 5-Cl-thien-3-yl | |
| 4-CF₃ | 4-OCF₂H | 5-Cl-thien-3-yl | |
| 4-CF₃ | 4-CF₃ | 5-Cl-thien-3-yl | |
| 4-CF₃ | 4-CN | 5-Cl-thien-3-yl | |
| 4-CF₃ | 4-OCF₃ | 5-Cl-thien-3-yl | |
| 4-CF₃ | 4-Cl | 5-F-thien-3-yl | |
| 4-CF₃ | 4-F | 5-F-thien-3-yl | |
| 4-CF₃ | 4-OCF₂H | 5-F-thien-3-yl | |
| 4-CF₃ | 4-CF₃ | 5-F-thien-3-yl | |
| 4-CF₃ | 4-CN | 5-F-thien-3-yl | |
| 4-CF₃ | 4-OCF₃ | 5-F-thien-3-yl | |
| 4-CF₃ | 4-Cl | 2-furyl | 167 to 171 |
| 4-CF₃ | 4-F | 2-furyl | |
| 4-CF₃ | 4-OCF₂H | 2-furyl | |
| 4-CF₃ | 4-CF₃ | 2-furyl | |
| 4-CF₃ | 4-CN | 2-furyl | |
| 4-CF₃ | 4-OCF₃ | 2-furyl | |
| 4-CF₃ | 4-Cl | 3-furyl | |
| 4-CF₃ | 4-F | 3-furyl | |
| 4-CF₃ | 4-OCF₂H | 3-furyl | |
| 4-CF₃ | 4-CF₃ | 3-furyl | |
| 4-CF₃ | 4-CN | 3-furyl | |
| 4-CF₃ | 4-OCF₃ | 3-furyl | |
| 4-CF₃ | 4-Cl | 5-Cl-fur-2-yl | |
| 4-CF₃ | 4-F | 5-Cl-fur-2-yl | |
| 4-CF₃ | 4-OCF₂H | 5-Cl-fur-2-yl | |
| 4-CF₃ | 4-CF₃ | 5-Cl-fur-2-yl | |
| 4-CF₃ | 4-CN | 5-Cl-fur-2-yl | |
| 4-CF₃ | 4-OCF₃ | 5-Cl-fur-2-yl | |
| 4-CF₃ | 4-Cl | 5-Cl-fur-3-yl | |
| 4-CF₃ | 4-F | 5-Cl-fur-3-yl | |
| 4-CF₃ | 4-OCF₂H | 5-Cl-fur-3-yl | |
| 4-CF₃ | 4-CF₃ | 5-Cl-fur-3-yl | |
| 4-CF₃ | 4-CN | 5-Cl-fur-3-yl | |
| 4-CF₃ | 4-OCF₃ | 5-Cl-fur-3-yl | |
| 4-CF₃ | 4-Cl | 2-pyrimidyl | |
| 4-CF₃ | 4-F | 2-pyrimidyl | |
| 4-CF₃ | 4-OCF₂H | 2-pyrimidyl | |
| 4-CF₃ | 4-CF₃ | 2-pyrimidyl | |
| 4-CF₃ | 4-CN | 2-pyrimidyl | |
| 4-CF₃ | 4-OCF₃ | 2-pyrimidyl | |
| 4-CF₃ | 4-Cl | 4-pyrimidyl | |
| 4-CF₃ | 4-F | 4-pyrimidyl | |
| 4-CF₃ | 4-OCF₂H | 4-pyrimidyl | |
| 4-CF₃ | 4-CF₃ | 4-pyrimidyl | |
| 4-CF₃ | 4-CN | 4-pyrimidyl | |
| 4-CF₃ | 4-OCF₃ | 4-pyrimidyl | |
| 4-CF₃ | 4-Cl | 5-pyrimidyl | |
| 4-CF₃ | 4-F | 5-pyrimidyl | |
| 4-CF₃ | 4-OCF₂H | 5-pyrimidyl | |
| 4-CF₃ | 4-CF₃ | 5-pyrimidyl | |
| 4-CF₃ | 4-CN | 5-pyrimidyl | |
| 4-CF₃ | 4-OCF₃ | 5-pyrimidyl | |
| 4-CF₃ | 4-Cl | 2-Cl-pyrimid-5-yl | |
| 4-CF₃ | 4-F | 2-Cl-pyrimid-5-yl | |
| 4-CF₃ | 4-OCF₂H | 2-Cl-pyrimid-5-yl | |
| 4-CF₃ | 4-CF₃ | 2-Cl-pyrimid-5-yl | |
| 4-CF₃ | 4-CN | 2-Cl-pyrimid-5-yl | |
| 4-CF₃ | 4-OCF₃ | 2-Cl-pyrimid-5-yl | |
| 4-CF₃ | 4-Cl | 2-pyrazinyl | |
| 4-CF₃ | 4-F | 2-pyrazinyl | |
| 4-CF₃ | 4-OCF₂H | 2-pyrazinyl | |
| 4-CF₃ | 4-CF₃ | 2-pyrazinyl | |
| 4-CF₃ | 4-CN | 2-pyrazinyl | |
| 4-CF₃ | 4-OCF₃ | 2-pyrazinyl | |
| 4-CF₃ | 4-Cl | 5-Cl-pyrazin-2-yl | |
| 4-CF₃ | 4-F | 5-Cl-pyrazin-2-yl | |

TABLE 1-continued

| R₁ | R₂ | J | (m.p. °C) |
|---|---|---|---|
| 4-CF₃ | 4-OCF₂H | 5-Cl-pyrazin-2-yl | |
| 4-CF₃ | 4-CF₃ | 5-Cl-pyrazin-2-yl | |
| 4-CF₃ | 4-CN | 5-Cl-pyrazin-2-yl | |
| 4-CF₃ | 4-OCF₃ | 5-Cl-pyrazin-2-yl | |
| 4-CF₃ | 4-Cl | 2-pyridazinyl | |
| 4-CF₃ | 4-F | 2-pyridazinyl | |
| 4-CF₃ | 4-OCF₂H | 2-pyridazinyl | |
| 4-CF₃ | 4-CF₃ | 2-pyridazinyl | |
| 4-CF₃ | 4-CN | 2-pyridazinyl | |
| 4-CF₃ | 4-OCF₃ | 2-pyridazinyl | |
| 4-CF₃ | 4-Cl | 2-thiazolyl | |
| 4-CF₃ | 4-F | 2-thiazolyl | |
| 4-CF₃ | 4-OCF₂H | 2-thiazolyl | |
| 4-CF₃ | 4-CF₃ | 2-thiazolyl | |
| 4-CF₃ | 4-CN | 2-thiazolyl | |
| 4-CF₃ | 4-OCF₃ | 2-thiazolyl | |
| 4-CF₃ | 4-Cl | 2-oxazolyl | |
| 4-CF₃ | 4-F | 2-oxazolyl | |
| 4-CF₃ | 4-OCF₂H | 2-oxazolyl | |
| 4-CF₃ | 4-CF₃ | 2-oxazolyl | |
| 4-CF₃ | 4-CN | 2-oxazolyl | |
| 4-CF₃ | 4-OCF₃ | 2-oxazolyl | |
| 4-CF₃ | 4-Cl | 1-Me-imidazol-2-yl | |
| 4-CF₃ | 4-F | 1-Me-imidazol-2-yl | |
| 4-CF₃ | 4-OCF₂H | 1-Me-imidazol-2-yl | |
| 4-CF₃ | 4-CF₃ | 1-Me-imidazol-2-yl | |
| 4-CF₃ | 4-CN | 1-Me-imidazol-2-yl | |
| 4-CF₃ | 4-OCF₃ | 1-Me-imidazol-2-yl | |
| 4-CF₃ | 4-Cl | 1-Me-imidazol-4-yl | |
| 4-CF₃ | 4-F | 1-Me-imidazol-4-yl | |
| 4-CF₃ | 4-OCF₂H | 1-Me-imidazol-4-yl | |
| 4-CF₃ | 4-CF₃ | 1-Me-imidazol-4-yl | |
| 4-CF₃ | 4-CN | 1-Me-imidazol-4-yl | |
| 4-CF₃ | 4-OCF₃ | 1-Me-imidazol-4-yl | |
| 4-OCF₃ | 4-Cl | 2-pyridyl | |
| 4-OCF₃ | 4-F | 2-pyridyl | |
| 4-OCF₃ | 4-OCF₂H | 2-pyridyl | |
| 4-OCF₃ | 4-CF₃ | 2-pyridyl | |
| 4-OCF₃ | 4-CN | 2-pyridyl | |
| 4-OCF₃ | 4-OCF₃ | 2-pyridyl | |
| 4-OCF₃ | 4-Cl | 3-pyridyl | |
| 4-OCF₃ | 4-F | 3-pyridyl | |
| 4-OCF₃ | 4-OCF₂H | 3-pyridyl | |
| 4-OCF₃ | 4-CF₃ | 3-pyridyl | |
| 4-OCF₃ | 4-CN | 3-pyridyl | |
| 4-OCF₃ | 4-OCF₃ | 3-pyridyl | |
| 4-OCF₃ | 4-Cl | 4-pyridyl | |
| 4-OCF₃ | 4-F | 4-pyridyl | |
| 4-OCF₃ | 4-OCF₂H | 4-pyridyl | |
| 4-OCF₃ | 4-CF₃ | 4-pyridyl | |
| 4-OCF₃ | 4-CN | 4-pyridyl | |
| 4-OCF₃ | 4-OCF₃ | 4-pyridyl | |
| 4-OCF₃ | 4-Cl | 5-Cl-pyrid-2-yl | |
| 4-OCF₃ | 4-F | 5-Cl-pyrid-2-yl | |
| 4-OCF₃ | 4-OCF₂H | 5-Cl-pyrid-2-yl | |
| 4-OCF₃ | 4-CF₃ | 5-Cl-pyrid-2-yl | |
| 4-OCF₃ | 4-CN | 5-Cl-pyrid-2-yl | |
| 4-OCF₃ | 4-OCF₃ | 5-Cl-pyrid-2-yl | |
| 4-OCF₃ | 4-Cl | 2-thienyl | |
| 4-OCF₃ | 4-F | 2-thienyl | |
| 4-OCF₃ | 4-OCF₂H | 2-thienyl | |
| 4-OCF₃ | 4-CF₃ | 2-thienyl | |
| 4-OCF₃ | 4-CN | 2-thienyl | |
| 4-OCF₃ | 4-OCF₃ | 2-thienyl | |
| 4-OCF₃ | 4-Cl | 3-thienyl | |
| 4-OCF₃ | 4-F | 3-thienyl | |
| 4-OCF₃ | 4-OCF₂H | 3-thienyl | |
| 4-OCF₃ | 4-CF₃ | 3-thienyl | |
| 4-OCF₃ | 4-CN | 3-thienyl | |
| 4-OCF₃ | 4-OCF₃ | 3-thienyl | |
| 4-OCF₃ | 4-Cl | 5-Cl-thien-2-yl | |
| 4-OCF₃ | 4-F | 5-Cl-thien-2-yl | |
| 4-OCF₃ | 4-OCF₂H | 5-Cl-thien-2-yl | |
| 4-OCF₃ | 4-CF₃ | 5-Cl-thien-2-yl | |
| 4-OCF₃ | 4-CN | 5-Cl-thien-2-yl | |
| 4-OCF₃ | 4-OCF₃ | 5-Cl-thien-2-yl | |
| 4-OCF₃ | 4-Cl | 5-Cl-thien-3-yl | |
| 4-OCF₃ | 4-F | 5-Cl-thien-3-yl | |
| 4-OCF₃ | 4-OCF₂H | 5-Cl-thien-3-yl | |
| 4-OCF₃ | 4-CF₃ | 5-Cl-thien-3-yl | |
| 4-OCF₃ | 4-CN | 5-Cl-thien-3-yl | |
| 4-OCF₃ | 4-OCF₃ | 5-Cl-thien-3-yl | |
| 4-OCF₃ | 4-Cl | 2-furyl | |
| 4-OCF₃ | 4-F | 2-furyl | |
| 4-OCF₃ | 4-OCF₂H | 2-furyl | |
| 4-OCF₃ | 4-CF₃ | 2-furyl | |
| 4-OCF₃ | 4-CN | 2-furyl | |
| 4-OCF₃ | 4-OCF₃ | 2-furyl | |
| 4-OCF₃ | 4-Cl | 3-furyl | |
| 4-OCF₃ | 4-F | 3-furyl | |
| 4-OCF₃ | 4-OCF₂H | 3-furyl | |
| 4-OCF₃ | 4-CF₃ | 3-furyl | |
| 4-OCF₃ | 4-CN | 3-furyl | |
| 4-OCF₃ | 4-OCF₃ | 3-furyl | |
| 4-OCF₃ | 4-Cl | 5-pyrimidyl | |
| 4-OCF₃ | 4-F | 5-pyrimidyl | |
| 4-OCF₃ | 4-OCF₂H | 5-pyrimidyl | |
| 4-OCF₃ | 4-CF₃ | 5-pyrimidyl | |
| 4-OCF₃ | 4-CN | 5-pyrimidyl | |
| 4-OCF₃ | 4-OCF₃ | 5-pyrimidyl | |
| 4-Cl | 4-Cl | 2-pyridyl | |
| 4-Cl | 4-F | 2-pyridyl | |
| 4-Cl | 4-OCF₂H | 2-pyridyl | |
| 4-Cl | 4-CF₃ | 2-pyridyl | |
| 4-Cl | 4-CN | 2-pyridyl | |
| 4-Cl | 4-OCF₃ | 2-pyridyl | |
| 4-Cl | 4-Cl | 4-pyridyl | |
| 4-Cl | 4-F | 4-pyridyl | |
| 4-Cl | 4-OCF₂H | 4-pyridyl | |
| 4-Cl | 4-CF₃ | 4-pyridyl | |
| 4-Cl | 4-CN | 4-pyridyl | |
| 4-Cl | 4-OCF₃ | 4-pyridyl | |
| 4-Cl | 4-Cl | 2-thienyl | |
| 4-Cl | 4-F | 2-thienyl | |
| 4-Cl | 4-OCF₂H | 2-thienyl | |
| 4-Cl | 4-CF₃ | 2-thienyl | |
| 4-Cl | 4-CN | 2-thienyl | |
| 4-Cl | 4-OCF₃ | 2-thienyl | |
| 4-Cl | 4-Cl | 3-thienyl | 215 to 217 |
| 4-Cl | 4-F | 3-thienyl | |
| 4-Cl | 4-OCF₂H | 3-thienyl | |
| 4-Cl | 4-CF₃ | 3-thienyl | |
| 4-Cl | 4-CN | 3-thienyl | |
| 4-Cl | 4-OCF₃ | 3-thienyl | |
| 4-Cl | 4-Cl | 5-Cl-thien-2-yl | |
| 4-Cl | 4-F | 5-Cl-thien-2-yl | |
| 4-Cl | 4-OCF₂H | 5-Cl-thien-2-yl | |
| 4-Cl | 4-CF₃ | 5-Cl-thien-2-yl | |
| 4-Cl | 4-CN | 5-Cl-thien-2-yl | |
| 4-Cl | 4-OCF₃ | 5-Cl-thien-2-yl | |
| 4-Cl | 4-Cl | 2-furyl | 187 to 188.5 |
| 4-Cl | 4-F | 2-furyl | |
| 4-Cl | 4-OCF₂H | 2-furyl | |
| 4-Cl | 4-CF₃ | 2-furyl | |
| 4-Cl | 4-CN | 2-furyl | |
| 4-Cl | 4-OCF₃ | 2-furyl | |
| 4-Cl | 4-Cl | 3-furyl | |
| 4-Cl | 4-F | 3-furyl | |
| 4-Cl | 4-OCF₂H | 3-furyl | |
| 4-Cl | 4-CF₃ | 3-furyl | |
| 4-Cl | 4-CN | 3-furyl | |
| 4-Cl | 4-OCF₃ | 3-furyl | |
| 4-Cl | 4-Cl | 5-pyrimidyl | |
| 4-Cl | 4-F | 5-pyrimidyl | |
| 4-Cl | 4-OCF₂H | 5-pyrimidyl | |
| 4-Cl | 4-CF₃ | 5-pyrimidyl | |
| 4-Cl | 4-CN | 5-pyrimidyl | |
| 4-Cl | 4-OCF₃ | 5-pyrimidyl | |
| 4-Br | 4-Cl | 2-pyridyl | |
| 4-Br | 4-F | 2-pyridyl | |
| 4-Br | 4-OCF₂H | 2-pyridyl | |
| 4-Br | 4-CF₃ | 2-pyridyl | |
| 4-Br | 4-CN | 2-pyridyl | |
| 4-Br | 4-OCF₃ | 2-pyridyl | |
| 4-Br | 4-Cl | 4-pyridyl | |
| 4-Br | 4-F | 4-pyridyl | |
| 4-Br | 4-OCF₂H | 4-pyridyl | |
| 4-Br | 4-CF₃ | 4-pyridyl | |
| 4-Br | 4-CN | 4-pyridyl | |
| 4-Br | 4-OCF₃ | 4-pyridyl | |
| 4-Br | 4-Cl | 2-thienyl | |
| 4-Br | 4-F | 2-thienyl | |

TABLE 1-continued

| R₁ | R₂ | J | (m p °C) |
|---|---|---|---|
| 4-Br | 4-OCF₂H | 2-thienyl | |
| 4-Br | 4-CF₃ | 2-thienyl | |
| 4-Br | 4-CN | 2-thienyl | |
| 4-Br | 4-OCF₃ | 2-thienyl | |
| 4-Br | 4-Cl | 3-thienyl | 220 to 222 |
| 4-Br | 4-F | 3-thienyl | |
| 4-Br | 4-OCF₂H | 3-thienyl | |
| 4-Br | 4-CF₃ | 3-thienyl | |
| 4-Br | 4-CN | 3-thienyl | |
| 4-Br | 4-OCF₃ | 3-thienyl | |
| 4-Br | 4-Cl | 5-Cl-thien-2-yl | |
| 4-Br | 4-F | 5-Cl-thien-2-yl | |
| 4-Br | 4-OCF₂H | 5-Cl-thien-2-yl | |
| 4-Br | 4-CF₃ | 5-Cl-thien-2-yl | |
| 4-Br | 4-CN | 5-Cl-thien-2-yl | |
| 4-Br | 4-OCF₃ | 5-Cl-thien-2-yl | |
| 4-Br | 4-Cl | 2-furyl | |
| 4-Br | 4-F | 2-furyl | |
| 4-Br | 4-OCF₂H | 2-furyl | |
| 4-Br | 4-CF₃ | 2-furyl | |
| 4-Br | 4-CN | 2-furyl | |
| 4-Br | 4-OCF₃ | 2-furyl | |
| 4-Br | 4-Cl | 3-furyl | |
| 4-Br | 4-F | 3-furyl | |
| 4-Br | 4-OCF₂H | 3-furyl | |
| 4-Br | 4-CF₃ | 3-furyl | |
| 4-Br | 4-CN | 3-furyl | |
| 4-Br | 4-OCF₃ | 3-furyl | |

TABLE 2

| R₁ | K | R₅ | (m p °C) |
|---|---|---|---|
| 4-CF₃ | 5-Cl-pyrid-2-yl | 4-F | 175 to 177 |
| 4-CF₃ | 5-Cl-pyrid-2-yl | 4-Cl | |
| 4-CF₃ | 5-Cl-pyrid-2-yl | 4-CN | |
| 4-CF₃ | 5-Cl-pyrid-2-yl | 4-CF₃ | |
| 4-CF₃ | 5-Cl-pyrid-2-yl | 3-Cl | |
| 4-CF₃ | 5-Cl-pyrid-2-yl | 3,4-di-F | |
| 4-CF₃ | 5-CF₃-pyrid-2-yl | 4-F | 180 to 182 |
| 4-CF₃ | 5-CF₃-pyrid-2-yl | 4-Cl | |
| 4-CF₃ | 5-CF₃-pyrid-2-yl | 4-CN | |
| 4-CF₃ | 5-CF₃-pyrid-2-yl | 4-CF₃ | |
| 4-CF₃ | 5-CF₃-pyrid-2-yl | 3-Cl | |
| 4-CF₃ | 5-CF₃-pyrid-2-yl | 3,4-di-F | |
| 4-CF₃ | 5-Br-pyrid-2-yl | 4-F | 199 to 200 |
| 4-CF₃ | 5-Br-pyrid-2-yl | 4-Cl | |
| 4-CF₃ | 5-Br-pyrid-2-yl | 4-CN | |
| 4-CF₃ | 5-Br-pyrid-2-yl | 4-CF₃ | |
| 4-CF₃ | 5-Br-pyrid-2-yl | 3-Cl | |
| 4-CF₃ | 5-Br-pyrid-2-yl | 3,4-di-F | |
| 4-CF₃ | 2-pyridyl | 4-F | |
| 4-CF₃ | 2-pyridyl | 4-Cl | |
| 4-CF₃ | 2-pyridyl | 4-CN | |
| 4-CF₃ | 2-pyridyl | 4-CF₃ | |
| 4-CF₃ | 2-pyridyl | 3-Cl | |
| 4-CF₃ | 2-pyridyl | 3,4-di-F | 168 to 170 |
| 4-CF₃ | 3-pyridyl | 4-F | 197 to 200 |
| 4-CF₃ | 3-pyridyl | 4-Cl | |
| 4-CF₃ | 3-pyridyl | 4-CN | |
| 4-CF₃ | 3-pyridyl | 4-CF₃ | |
| 4-CF₃ | 3-pyridyl | 3-Cl | |
| 4-CF₃ | 3-pyridyl | 3,4-di-F | |
| 4-CF₃ | 2-Cl-pyrid-5-yl | 4-F | |
| 4-CF₃ | 2-Cl-pyrid-5-yl | 4-Cl | |
| 4-CF₃ | 2-Cl-pyrid-5-yl | 4-CN | |
| 4-CF₃ | 2-Cl-pyrid-5-yl | 4-CF₃ | |
| 4-CF₃ | 2-Cl-pyrid-5-yl | 3-Cl | |
| 4-CF₃ | 2-Cl-pyrid-5-yl | 3,4-di-F | |
| 4-CF₃ | 4-pyridyl | 4-F | |
| 4-CF₃ | 4-pyridyl | 4-Cl | |
| 4-CF₃ | 4-pyridyl | 4-CN | |
| 4-CF₃ | 4-pyridyl | 4-CF₃ | |
| 4-CF₃ | 4-pyridyl | 3-Cl | |
| 4-CF₃ | 4-pyridyl | 3,4-di-F | |
| 4-CF₃ | 2-pyrimidyl | 4-F | 220 to 221 |
| 4-CF₃ | 2-pyrimidyl | 4-Cl | |
| 4-CF₃ | 2-pyrimidyl | 4-CN | |
| 4-CF₃ | 2-pyrimidyl | 4-CF₃ | |
| 4-CF₃ | 2-pyrimidyl | 3-Cl | |

TABLE 2-continued

| R₁ | K | R₅ | (m p °C) |
|---|---|---|---|
| 4-CF₃ | 2-pyrimidyl | 3,4-di-F | 196 to 199 |
| 4-CF₃ | 4-pyrimidyl | 4-F | |
| 4-CF₃ | 4-pyrimidyl | 4-Cl | |
| 4-CF₃ | 4-pyrimidyl | 4-CN | |
| 4-CF₃ | 4-pyrimidyl | 4-CF₃ | |
| 4-CF₃ | 4-pyrimidyl | 3-Cl | |
| 4-CF₃ | 4-pyrimidyl | 3,4-di-F | |
| 4-CF₃ | 5-Cl-pyrimid-2-yl | 4-F | 195 to 200 |
| 4-CF₃ | 5-Cl-pyrimid-2-yl | 4-Cl | |
| 4-CF₃ | 5-Cl-pyrimid-2-yl | 4-CN | |
| 4-CF₃ | 5-Cl-pyrimid-2-yl | 4-CF₃ | |
| 4-CF₃ | 5-Cl-pyrimid-2-yl | 3-Cl | |
| 4-CF₃ | 5-Cl-pyrimid-2-yl | 3,4-di-F | 103 to 106 |
| 4-CF₃ | 2-pyrazinyl | 4-F | |
| 4-CF₃ | 2-pyrazinyl | 4-Cl | |
| 4-CF₃ | 2-pyrazinyl | 4-CN | |
| 4-CF₃ | 2-pyrazinyl | 4-CF₃ | |
| 4-CF₃ | 2-pyrazinyl | 3-Cl | |
| 4-CF₃ | 2-pyrazinyl | 3,4-di-F | |
| 4-CF₃ | 3-pyridazinyl | 4-F | |
| 4-CF₃ | 3-pyridazinyl | 4-Cl | |
| 4-CF₃ | 3-pyridazinyl | 4-CN | |
| 4-CF₃ | 3-pyridazinyl | 4-CF₃ | |
| 4-CF₃ | 3-pyridazinyl | 3-Cl | |
| 4-CF₃ | 3-pyridazinyl | 3,4-di-F | |
| 4-CF₃ | 6-Cl-pyridazin-3-yl | 4-F | 200 to 202 |
| 4-CF₃ | 6-Cl-pyridazin-3-yl | 4-Cl | |
| 4-CF₃ | 6-Cl-pyridazin-3-yl | 4-CN | |
| 4-CF₃ | 6-Cl-pyridazin-3-yl | 4-CF₃ | |
| 4-CF₃ | 6-Cl-pyridazin-3-yl | 3-Cl | |
| 4-CF₃ | 6-Cl-pyridazin-3-yl | 3,4-di-F | |
| 4-CF₃ | 2-thiazolyl | 4-F | |
| 4-CF₃ | 2-thiazolyl | 4-Cl | |
| 4-CF₃ | 2-thiazolyl | 4-CN | |
| 4-CF₃ | 2-thiazolyl | 4-CF₃ | |
| 4-CF₃ | 2-thiazolyl | 3-Cl | |
| 4-CF₃ | 2-thiazolyl | 3,4-di-F | |
| 4-CF₃ | 2-oxazolyl | 4-F | |
| 4-CF₃ | 2-oxazolyl | 4-Cl | |
| 4-CF₃ | 2-oxazolyl | 4-CN | |
| 4-CF₃ | 2-oxazolyl | 4-CF₃ | |
| 4-CF₃ | 2-oxazolyl | 3-Cl | |
| 4-CF₃ | 2-oxazolyl | 3,4-di-F | |
| 4-CF₃ | 1-Me-imidazol-2-yl | 4-F | |
| 4-CF₃ | 1-Me-imidazol-2-yl | 4-Cl | |
| 4-CF₃ | 1-Me-imidazol-2-yl | 4-CN | |
| 4-CF₃ | 1-Me-imidazol-2-yl | 4-CF₃ | |
| 4-CF₃ | 1-Me-imidazol-2-yl | 3-Cl | |
| 4-CF₃ | 1-Me-imidazol-2-yl | 3,4-di-F | |
| 4-CF₃ | 2-thienyl | 4-F | |
| 4-CF₃ | 2-thienyl | 4-Cl | |
| 4-CF₃ | 2-thienyl | 4-CN | |
| 4-CF₃ | 2-thienyl | 4-CF₃ | |
| 4-CF₃ | 2-thienyl | 3-Cl | |
| 4-CF₃ | 2-thienyl | 3,4-di-F | |
| 4-CF₃ | 2-furyl | 4-F | |
| 4-CF₃ | 2-furyl | 4-Cl | |
| 4-CF₃ | 2-furyl | 4-CN | |
| 4-CF₃ | 2-furyl | 4-CF₃ | |
| 4-CF₃ | 2-furyl | 3-Cl | |
| 4-CF₃ | 2-furyl | 3,4-di-F | |
| 4-OCF₃ | 5-Cl-pyrid-2-yl | 4-F | |
| 4-OCF₃ | 5-Cl-pyrid-2-yl | 4-Cl | |
| 4-OCF₃ | 5-Cl-pyrid-2-yl | 4-CN | |
| 4-OCF₃ | 5-Cl-pyrid-2-yl | 4-CF₃ | |
| 4-OCF₃ | 5-Cl-pyrid-2-yl | 3-Cl | |
| 4-OCF₃ | 5-Cl-pyrid-2-yl | 3,4-di-F | |
| 4-OCF₃ | 5-CF₃-pyrid-2-yl | 4-F | |
| 4-OCF₃ | 5-CF₃-pyrid-2-yl | 4-Cl | |
| 4-OCF₃ | 5-CF₃-pyrid-2-yl | 4-CN | |
| 4-OCF₃ | 5-CF₃-pyrid-2-yl | 4-CF₃ | |
| 4-OCF₃ | 5-CF₃-pyrid-2-yl | 3-Cl | |
| 4-OCF₃ | 5-CF₃-pyrid-2-yl | 3,4-di-F | |
| 4-OCF₃ | 2-pyridyl | 4-F | |
| 4-OCF₃ | 2-pyridyl | 4-Cl | |
| 4-OCF₃ | 2-pyridyl | 4-CN | |
| 4-OCF₃ | 2-pyridyl | 4-CF₃ | |
| 4-OCF₃ | 2-pyridyl | 3-Cl | |
| 4-OCF₃ | 2-pyridyl | 3,4-di-F | |
| 4-OCF₃ | 3-pyridyl | 4-F | |
| 4-OCF₃ | 3-pyridyl | 4-Cl | |

TABLE 2-continued

| R₁ | K | R₅ | (m.p. °C) |
|---|---|---|---|
| 4-OCF₃ | 3-pyridyl | 4-CN | |
| 4-OCF₃ | 3-pyridyl | 4-CF₃ | |
| 4-OCF₃ | 3-pyridyl | 3-Cl | |
| 4-OCF₃ | 3-pyridyl | 3,4-di-F | |
| 4-OCF₃ | 5-Cl-pyrimid-2-yl | 4-F | |
| 4-OCF₃ | 5-Cl-pyrimid-2-yl | 4-Cl | |
| 4-OCF₃ | 5-Cl-pyrimid-2-yl | 4-CN | |
| 4-OCF₃ | 5-Cl-pyrimid-2-yl | 4-CF₃ | |
| 4-OCF₃ | 5-Cl-pyrimid-2-yl | 3-Cl | |
| 4-OCF₃ | 5-Cl-pyrimid-2-yl | 3,4-di-F | |
| 4-OCF₃ | 4-pyrimidyl | 4-F | |
| 4-OCF₃ | 4-pyrimidyl | 4-Cl | |
| 4-OCF₃ | 4-pyrimidyl | 4-CN | |
| 4-OCF₃ | 4-pyrimidyl | 4-CF₃ | |
| 4-OCF₃ | 4-pyrimidyl | 3-Cl | |
| 4-OCF₃ | 4-pyrimidyl | 3,4-di-F | |
| 4-OCF₃ | 6-Cl-pyridazin-3-yl | 4-F | |
| 4-OCF₃ | 6-Cl-pyridazin-3-yl | 4-Cl | |
| 4-OCF₃ | 6-Cl-pyridazin-3-yl | 4-CN | |
| 4-OCF₃ | 6-Cl-pyridazin-3-yl | 4-CF₃ | |
| 4-OCF₃ | 6-Cl-pyridazin-3-yl | 3-Cl | |
| 4-OCF₃ | 6-Cl-pyridazin-3-yl | 3,4-di-F | |
| 4-Cl | 5-Cl-pyrid-2-yl | 4-F | |
| 4-Cl | 5-Cl-pyrid-2-yl | 4-Cl | |
| 4-Cl | 5-Cl-pyrid-2-yl | 4-CN | |
| 4-Cl | 5-Cl-pyrid-2-yl | 4-CF₃ | |
| 4-Cl | 5-Cl-pyrid-2-yl | 3-Cl | |
| 4-Cl | 5-Cl-pyrid-2-yl | 3,4-di-F | |
| 4-Cl | 5-CF₃-pyrid-2-yl | 4-F | |
| 4-Cl | 5-CF₃-pyrid-2-yl | 4-Cl | |
| 4-Cl | 5-CF₃-pyrid-2-yl | 4-CN | |
| 4-Cl | 5-CF₃-pyrid-2-yl | 4-CF₃ | |
| 4-Cl | 5-CF₃-pyrid-2-yl | 3-Cl | |
| 4-Cl | 5-CF₃-pyrid-2-yl | 3,4-di-F | |
| 4-Cl | 3-pyridyl | 4-F | 95 |
| 4-Cl | 3-pyridyl | 4-Cl | |
| 4-Cl | 3-pyridyl | 4-CN | |
| 4-Cl | 3-pyridyl | 4-CF₃ | |
| 4-Cl | 3-pyridyl | 3-Cl | |
| 4-Cl | 3-pyridyl | 3,4-di-F | |
| 4-Cl | 6-Cl-pyridazin-3-yl | 4-F | 207 to 210 |
| 4-Cl | 6-Cl-pyridazin-3-yl | 4-Cl | |
| 4-Cl | 6-Cl-pyridazin-3-yl | 4-CN | |
| 4-Cl | 6-Cl-pyridazin-3-yl | 4-CF₃ | |
| 4-Cl | 6-Cl-pyridazin-3-yl | 3-Cl | |
| 4-Cl | 6-Cl-pyridazin-3-yl | 3,4-di-F | |
| 4-Cl | 5-Cl-pyrimid-2-yl | 4-F | |
| 4-Cl | 5-Cl-pyrimid-2-yl | 4-Cl | |
| 4-Cl | 5-Cl-pyrimid-2-yl | 4-CN | |
| 4-Cl | 5-Cl-pyrimid-2-yl | 4-CF₃ | |
| 4-Cl | 5-Cl-pyrimid-2-yl | 3-Cl | |
| 4-Cl | 5-Cl-pyrimid-2-yl | 3,4-di-F | |
| 4-Br | 5-Cl-pyrid-2-yl | 4-F | |
| 4-Br | 5-Cl-pyrid-2-yl | 4-Cl | |
| 4-Br | 5-Cl-pyrid-2-yl | 4-CN | |
| 4-Br | 5-Cl-pyrid-2-yl | 4-CF₃ | |
| 4-Br | 5-Cl-pyrid-2-yl | 3-Cl | |
| 4-Br | 5-Cl-pyrid-2-yl | 3,4-di-F | |
| 4-Br | 5-CF₃-pyrid-2-yl | 4-F | |
| 4-Br | 5-CF₃-pyrid-2-yl | 4-Cl | |
| 4-Br | 5-CF₃-pyrid-2-yl | 4-CN | |
| 4-Br | 5-CF₃-pyrid-2-yl | 4-CF₃ | |
| 4-Br | 5-CF₃-pyrid-2-yl | 3-Cl | |
| 4-Br | 5-CF₃-pyrid-2-yl | 3,4-di-F | |
| 4-Br | 6-Cl-pyridazin-3-yl | 4-F | 244 to 245 |
| 4-Br | 6-Cl-pyridazin-3-yl | 4-Cl | |
| 4-Br | 6-Cl-pyridazin-3-yl | 4-CN | |
| 4-Br | 6-Cl-pyridazin-3-yl | 4-CF₃ | |
| 4-Br | 6-Cl-pyridazin-3-yl | 3-Cl | |
| 4-Br | 6-Cl-pyridazin-3-yl | 3,4-di-F | |
| 4-CF₃ | 5-Br-pyrimid-2-yl | 4-F | 196 to 198 |

TABLE 3

| R₁ | K | B | A | Y | (m.p. °C) |
|---|---|---|---|---|---|
| 4-CF₃ | 2-pyridyl | CH₃ | CO₂Me | H | |
| 4-CF₃ | 3-pyridyl | CH₃ | CO₂Me | H | |
| 4-CF₃ | 4-pyridyl | CH₃ | CO₂Me | H | |
| 4-CF₃ | 5-Cl-pyrid-2-yl | CH₃ | CO₂Me | H | |
| 4-CF₃ | 5-CF₃-pyrid-2-yl | CH₃ | CO₂Me | H | |
| 4-CF₃ | 2-Cl-pyrid-5-yl | CH₃ | CO₂Me | H | |
| 4-CF₃ | 2-pyrimidyl | CH₃ | CO₂Me | H | |
| 4-CF₃ | 4-pyrimidyl | CH₃ | CO₂Me | H | |
| 4-CF₃ | 5-Cl-pyrimid-2-yl | CH₃ | CO₂Me | H | |
| 4-CF₃ | 2-pyrazinyl | CH₃ | CO₂Me | H | |
| 4-CF₃ | 3-pyridazinyl | CH₃ | CO₂Me | H | |
| 4-CF₃ | 6-Cl-pyridazin-3-yl | CH₃ | CO₂Me | H | |
| 4-CF₃ | 2-thiazolyl | CH₃ | CO₂Me | H | |
| 4-CF₃ | 2-oxazolyl | CH₃ | CO₂Me | H | |
| 4-CF₃ | 1-Me-imidazol-2-yl | CH₃ | CO₂Me | H | |
| 4-CF₃ | 2-thienyl | CH₃ | CO₂Me | H | |
| 4-CF₃ | 2-furyl | CH₃ | CO₂Me | H | |
| 4-CF₃ | 2-pyridyl | CH₃ | CO₂Me | CH₃ | |
| 4-CF₃ | 4-pyridyl | CH₃ | CO₂Me | CH₃ | |
| 4-CF₃ | 2-Cl-pyrid-5-yl | CH₃ | CO₂Me | CH₃ | |
| 4-CF₃ | 5-Cl-pyrid-2-yl | CH₃ | CO₂Me | CH₃ | |
| 4-CF₃ | 5-CF₃-pyrid-2-yl | CH₃ | CO₂Me | CH₃ | |
| 4-CF₃ | 4-pyrimidyl | CH₃ | CO₂Me | CH₃ | |
| 4-CF₃ | 6-Cl-pyridazin-3-yl | CH₃ | CO₂Me | CH₃ | |
| 4-Cl | 2-pyridyl | CH₃ | CO₂Me | H | |
| 4-Cl | 3-pyridyl | CH₃ | CO₂Me | H | |
| 4-Cl | 4-pyridyl | CH₃ | CO₂Me | H | |
| 4-Cl | 5-Cl-pyrid-2-yl | CH₃ | CO₂Me | H | |
| 4-Cl | 5-CF₃-pyrid-2-yl | CH₃ | CO₂Me | H | |
| 4-Cl | 2-Cl-pyrid-5-yl | CH₃ | CO₂Me | H | |
| 4-Cl | 2-pyrimidyl | CH₃ | CO₂Me | H | |
| 4-Cl | 4-pyrimidyl | CH₃ | CO₂Me | H | |
| 4-Cl | 5-Cl-pyrimid-2-yl | CH₃ | CO₂Me | H | |
| 4-Cl | 2-pyrazinyl | CH₃ | CO₂Me | H | |
| 4-Cl | 3-pyridazinyl | CH₃ | CO₂Me | H | |
| 4-Cl | 6-Cl-pyridazin-3-yl | CH₃ | CO₂Me | H | |
| 4-Cl | 2-thiazolyl | CH₃ | CO₂Me | H | |
| 4-Cl | 2-oxazolyl | CH₃ | CO₂Me | H | |
| 4-Cl | 1-Me-imidazol-2-yl | CH₃ | CO₂Me | H | |
| 4-Cl | 2-thienyl | CH₃ | CO₂Me | H | |
| 4-Cl | 2-furyl | CH₃ | CO₂Me | H | |
| 4-Cl | 2-pyridyl | CH₃ | CO₂Me | CH₃ | |
| 4-Cl | 4-pyridyl | CH₃ | CO₂Me | CH₃ | |
| 4-Cl | 2-Cl-pyrid-3-yl | CH₃ | CO₂Me | CH₃ | |
| 4-Cl | 5-Cl-pyrid-2-yl | CH₃ | CO₂Me | CH₃ | |
| 4-Cl | 5-CF₃-pyrid-2-yl | CH₃ | CO₂Me | CH₃ | |
| 4-Cl | 4-pyrimidyl | CH₃ | CO₂Me | CH₃ | |
| 4-Cl | 6-Cl-pyridazin-3-yl | CH₃ | CO₂Me | CH₃ | |
| 4-OCF₃ | 2-pyridyl | CH₃ | CO₂Me | H | |
| 4-OCF₃ | 3-pyridyl | CH₃ | CO₂Me | H | |
| 4-OCF₃ | 4-pyridyl | CH₃ | CO₂Me | H | |
| 4-OCF₃ | 5-Cl-pyrid-2-yl | CH₃ | CO₂Me | H | |
| 4-OCF₃ | 5-CF₃-pyrid-2-yl | CH₃ | CO₂Me | H | |
| 4-OCF₃ | 2-Cl-pyrid-5-yl | CH₃ | CO₂Me | H | |
| 4-OCF₃ | 2-pyrimidyl | CH₃ | CO₂Me | H | |
| 4-OCF₃ | 4-pyrimidyl | CH₃ | CO₂Me | H | |
| 4-OCF₃ | 5-Cl-pyrimid-2-yl | CH₃ | CO₂Me | H | |
| 4-OCF₃ | 2-pyrazinyl | CH₃ | CO₂Me | H | |
| 4-OCF₃ | 3-pyridazinyl | CH₃ | CO₂Me | H | |
| 4-OCF₃ | 6-Cl-pyridazin-3-yl | CH₃ | CO₂Me | H | |
| 4-OCF₃ | 2-thiazolyl | CH₃ | CO₂Me | H | |
| 4-OCF₃ | 2-oxazolyl | CH₃ | CO₂Me | H | |
| 4-OCF₃ | 1-Me-imidazol-2-yl | CH₃ | CO₂Me | H | |
| 4-OCF₃ | 2-thienyl | CH₃ | CO₂Me | H | |
| 4-OCF₃ | 2-furyl | CH₃ | CO₂Me | H | |
| 4-OCF₃ | 2-pyridyl | CH₃ | CO₂Me | CH₃ | |
| 4-OCF₃ | 4-pyridyl | CH₃ | CO₂Me | CH₃ | |
| 4-OCF₃ | 2-Cl-pyrid-3-yl | CH₃ | CO₂Me | CH₃ | |
| 4-OCF₃ | 5-Cl-pyrid-2-yl | CH₃ | CO₂Me | CH₃ | |
| 4-OCF₃ | 5-CF₃-pyrid-2-yl | CH₃ | CO₂Me | CH₃ | |
| 4-OCF₃ | 4-pyrimidyl | CH₃ | CO₂Me | CH₃ | |
| 4-OCF₃ | 6-Cl-pyridazin-3-yl | CH₃ | CO₂Me | CH₃ | |

TABLE 4

| R₁ | R₂ | J | X | Y | B | (m.p. °C) |
|---|---|---|---|---|---|---|
| 4-CF₃ | 4-Cl | 2-thienyl | S | H | H | |
| 4-CF₃ | 4-Cl | 3-thienyl | S | H | H | |

TABLE 4-continued

| R₁ | R₂ | J | X | Y | B | (m.p.°C.) |
|---|---|---|---|---|---|---|
| 4-CF₃ | 4-Cl | 5-Cl-thien-2-yl | S | H | H | |
| 4-CF₃ | 4-Cl | 5-Cl-pyrid-2-yl | S | H | H | |
| 4-CF₃ | 4-Cl | 2-furyl | S | H | H | |
| 4-CF₃ | 4-Cl | 3-furyl | S | H | H | |
| 4-CF₃ | 4-Cl | 2-thienyl | O | H | CH₃ | |
| 4-CF₃ | 4-Cl | 3-thienyl | O | H | CH₃ | |
| 4-CF₃ | 4-Cl | 5-Cl-thien-2-yl | O | H | CH₃ | |
| 4-CF₃ | 4-Cl | 5-Cl-pyrid-2-yl | O | H | CH₃ | |
| 4-CF₃ | 4-Cl | 2-furyl | O | H | CH₃ | |
| 4-CF₃ | 4-Cl | 3-furyl | O | H | CH₃ | |
| 4-CF₃ | 4-Cl | 2-thienyl | O | CH₃ | H | |
| 4-CF₃ | 4-Cl | 3-thienyl | O | CH₃ | H | |
| 4-CF₃ | 4-Cl | 5-Cl-thien-2-yl | O | CH₃ | H | |
| 4-CF₃ | 4-Cl | 5-Cl-pyrid-2-yl | O | CH₃ | H | |
| 4-CF₃ | 4-Cl | 2-furyl | O | CH₃ | H | |
| 4-CF₃ | 4-Cl | 3-furyl | O | CH₃ | H | |
| 4-CF₃ | 4-Cl | 2-thienyl | O | COCH₃ | H | |
| 4-CF₃ | 4-Cl | 3-thienyl | O | COCH₃ | H | |
| 4-CF₃ | 4-Cl | 5-Cl-thien-2-yl | O | COCH₃ | H | |
| 4-CF₃ | 4-Cl | 5-Cl-pyrid-2-yl | O | COCH₃ | H | |
| 4-CF₃ | 4-Cl | 2-furyl | O | COCH₃ | H | |
| 4-CF₃ | 4-Cl | 3-furyl | O | COCH₃ | H | |
| 4-CF₃ | 4-Cl | 2-thienyl | O | CO₂Me | H | |
| 4-CF₃ | 4-Cl | 3-thienyl | O | CO₂Me | H | |
| 4-CF₃ | 4-Cl | 5-Cl-thien-2-yl | O | CO₂Me | H | |
| 4-CF₃ | 4-Cl | 5-Cl-pyrid-2-yl | O | CO₂Me | H | |
| 4-CF₃ | 4-Cl | 2-furyl | O | CO₂Me | H | |
| 4-CF₃ | 4-Cl | 3-furyl | O | CO₂Me | H | |
| 4-CF₃ | 4-Cl | 5-Cl-thien-2-yl | S | H | CH₃ | |
| 4-CF₃ | 4-Cl | 5-Cl-thien-2-yl | S | CH₃ | H | |
| 4-CF₃ | 4-Cl | 5-Cl-thien-2-yl | S | CH₃ | CH₃ | |
| 4-CF₃ | 4-Cl | 5-Cl-pyrid-2-yl | O | H | Me | 146 to 148 |
| 4-OCF₃ | 4-Cl | 5-Cl-pyrid-2-yl | O | H | Me | |
| 4-I | 4-Cl | 5-Cl-pyrid-2-yl | O | H | Me | 192 to 195 |
| 4-Br | 4-Cl | 5-Cl-pyrid-2-yl | O | H | Me | 170 to 173 |
| 4-CF₃ | 4-Cl | 5-Br-pyrid-2-yl | O | H | Me | 162 to 165 |
| 4-OCF₃ | 4-Cl | 5-Br-pyrid-2-yl | O | H | Me | 161 to 163 |
| 4-Cl | 4-Cl | 5-Br-pyrid-2-yl | O | H | Me | 158 to 161 |
| 4-Br | 4-Cl | 5-Br-pyrid-2-yl | O | H | Me | 175 to 178 |
| 4-CF₃ | 4-Cl | 5-Br-thien-2-yl | O | H | Me | 182 to 185 |
| 4-OCF₃ | 4-Cl | 5-Br-thien-2-yl | O | H | Me | |
| 4-Cl | 4-Cl | 5-Br-thien-2-yl | O | H | Me | |
| 4-Br | 4-Cl | 5-Br-thien-2-yl | O | H | Me | 142 to 144 |
| 4-CF₃ | 4-Cl | 6-Cl-pyrid-2-yl | O | H | Me | 101.5 to 105 |
| 4-OCF₃ | 4-Cl | 6-Cl-pyrid-2-yl | O | H | Me | 108 to 110.5 |
| 4-Cl | 4-Cl | 6-Cl-pyrid-2-yl | O | H | Me | 132 to 134 |
| 4-Br | 4-Cl | 6-Cl-pyrid-2-yl | O | H | Me | |
| 4-CF₃ | 4-Cl | 6-Br-pyrid-2-yl | O | H | Me | foam (a) |
| 4-OCF₃ | 4-Cl | 6-Br-pyrid-2-yl | O | H | Me | gum (b) |
| 4-Cl | 4-Cl | 6-Br-pyrid-2-yl | O | H | Me | foam (c) |
| 4-Br | 4-Cl | 6-Br-pyrid-2-yl | O | H | Me | 91.5 to 95 |
| 4-CF₃ | 4-Cl | 5-Cl-pyrid-2-yl | O | Me | Me | 126 to 128 |
| 4-CF₃ | 4-Cl | 5-Br-pyrid-2-yl | O | Me | Me | 115 to 119 |
| 4-CF₃ | 4-Cl | 6-Cl-pyrid-2-yl | O | Me | Me | 105 to 107.5 |
| 4-CF₃ | 4-Cl | 5-Br-thien-2-yl | O | Me | Me | 156 to 159 |
| 4-CF₃ | 4-Cl | 6-Br-pyrid-2-yl | O | Me | Me | gum (d) |
| 4-CF₃ | 4-Cl | 5-Cl-thien-2-yl | O | S—N(Me)CO₂nBu | H | |
| 4-CF₃ | 4-Cl | 5-Cl-pyrid-2-yl | O | S—N(Me)CO₂nBu | H | |
| 4-CF₃ | 4-Cl | 5-Br-pyrid-2-yl | O | S—N(Me)CO₂nBu | H | |
| 4-CF₃ | 4-Cl | 6-Br-pyrid-2-yl | O | S—N(Me)CO₂nBu | H | |
| 4-CF₃ | 4-Cl | 5-Cl-thien-2-yl | O | S—N(i-Pr)CO₂Et | H | |
| 4-CF₃ | 4-Cl | 5-Cl-pyrid-2-yl | O | S—N(i-Pr)CO₂Et | H | |
| 4-CF₃ | 4-Cl | 5-Br-pyrid-2-yl | O | S—N(i-Pr)CO₂Et | H | |
| 4-CF₃ | 4-Cl | 6-Br-pyrid-2-yl | O | S—N(i-Pr)CO₂Et | H | |
| 4-CF₃ | 4-Cl | 5-Cl-thien-2-yl | O | S—N(Me)CO₂n-dec | H | |
| 4-CF₃ | 4-Cl | 5-Cl-pyrid-2-yl | O | S—N(Me)CO₂n-dec | H | |
| 4-CF₃ | 4-Cl | 5-Br-pyrid-2-yl | O | S—N(Me)CO₂n-dec | H | |
| 4-CF₃ | 4-Cl | 6-Br-pyrid-2-yl | O | S—N(Me)CO₂n-dec | H | |
| 4-CF₃ | 4-Cl | 5-Cl-thien-2-yl | O | S—N(Me)SO₂Ph | H | |
| 4-CF₃ | 4-Cl | 5-Cl-pyrid-2-yl | O | S—N(Me)SO₂Ph | H | |
| 4-CF₃ | 4-Cl | 5-Br-pyrid-2-yl | O | S—N(Me)SO₂Ph | H | |
| 4-CF₃ | 4-Cl | 6-Br-pyrid-2-yl | O | S—N(Me)SO₂Ph | H | |
| 4-CF₃ | 4-Cl | 5-Cl-thien-2-yl | O | S—CO₂-i-Bu | H | |
| 4-CF₃ | 4-Cl | 5-Cl-pyrid-2-yl | O | S—CO₂-i-Bu | H | |
| 4-CF₃ | 4-Cl | 5-Br-pyrid-2-yl | O | S—CO₂-i-Bu | H | |
| 4-CF₃ | 4-Cl | 6-Br-pyrid-2-yl | O | S—CO₂-i-Bu | H | |
| 4-CF₃ | 4-Cl | 5-Cl-thien-2-yl | O | S—P(O)(OEt)₂ | H | |
| 4-CF₃ | 4-Cl | 5-Cl-pyrid-2-yl | O | S—P(O)(OEt)₂ | H | |
| 4-CF₃ | 4-Cl | 5-Br-pyrid-2-yl | O | S—P(O)(OEt)₂ | H | |

TABLE 4-continued

| R₁ | R₂ | J | X | Y | B | (m.p °C.) |
|---|---|---|---|---|---|---|
| 4-CF₃ | 4-Cl | 6-Br-pyrid-2-yl | O | S—P(O)(OEt)₂ | H | |

(a) ν max = 1670, (b) ν max = 1670, (c) ν max = 1670, (d) ν max = 1640
I.R. Carbonyl absorptions

TABLE 5

| R₁ | K | R₅ | X | Y | B | (m.p °C.) |
|---|---|---|---|---|---|---|
| 4-CF₃ | 2-pyridyl | 4-F | S | H | H | |
| 4-CF₃ | 5-Cl-pyrid-2-yl | 4-F | S | H | H | |
| 4-CF₃ | 5-CF₃-pyrid-2-yl | 4-F | S | H | H | |
| 4-CF₃ | 3-pyridyl | 4-F | S | H | H | |
| 4-CF₃ | 4-pyridyl | 4-F | S | H | H | |
| 4-CF₃ | 6-Cl-pyridazin-3-yl | 4-F | S | H | H | |
| 4-CF₃ | 4-pyrimidyl | 4-F | S | H | H | |
| 4-CF₃ | 2-pyridyl | 4-F | O | H | CH₃ | |
| 4-CF₃ | 5-Cl-pyrid-2-yl | 4-F | O | H | CH₃ | |
| 4-CF₃ | 5-CF₃-pyrid-2-yl | 4-F | O | H | CH₃ | |
| 4-CF₃ | 3-pyridyl | 4-F | O | H | CH₃ | |
| 4-CF₃ | 4-pyridyl | 4-F | O | H | CH₃ | |
| 4-CF₃ | 6-Cl-pyridazin-3-yl | 4-F | O | H | CH₃ | |
| 4-CF₃ | 4-pyrimidyl | 4-F | O | H | CH₃ | |
| 4-CF₃ | 2-pyridyl | 4-F | O | CH₃ | H | |
| 4-CF₃ | 5-Cl-pyrid-2-yl | 4-F | O | CH₃ | H | |
| 4-CF₃ | 5-CF₃-pyrid-2-yl | 4-F | O | CH₃ | H | |
| 4-CF₃ | 3-pyridyl | 4-F | O | CH₃ | H | |
| 4-CF₃ | 4-pyridyl | 4-F | O | CH₃ | H | |
| 4-CF₃ | 6-Cl-pyridazin-3-yl | 4-F | O | CH₃ | H | |
| 4-CF₃ | 2-pyridyl | 4-F | O | COCH₃ | H | |
| 4-CF₃ | 5-Cl-pyrid-2-yl | 4-F | O | COCH₃ | H | |
| 4-CF₃ | 5-CF₃-pyrid-2-yl | 4-F | O | COCH₃ | H | |
| 4-CF₃ | 3-pyridyl | 4-F | O | COCH₃ | H | |
| 4-CF₃ | 4-pyridyl | 4-F | O | COCH₃ | H | |
| 4-CF₃ | 6-Cl-pyridazin-3-yl | 4-F | O | COCH₃ | H | |
| 4-CF₃ | 4-pyrimidyl | 4-F | O | COCH₃ | H | |
| 4-CF₃ | 2-pyridyl | 4-F | O | CO₂Me | H | |
| 4-CF₃ | 5-Cl-pyrid-2-yl | 4-F | O | CO₂Me | H | |
| 4-CF₃ | 5-CF₃-pyrid-2-yl | 4-F | O | CO₂Me | H | |
| 4-CF₃ | 3-pyridyl | 4-F | O | CO₂Me | H | |
| 4-CF₃ | 4-pyridyl | 4-F | O | CO₂Me | H | |
| 4-CF₃ | 6-Cl-pyridazin-3-yl | 4-F | O | CO₂Me | H | |
| 4-CF₃ | 4-pyrimidinyl | 4-F | O | CO₂Me | H | |
| 4-CF₃ | 5-Cl-pyrid-2-yl | 4-F | S | CO₂Me | CH₃ | |
| 4-CF₃ | 5-Cl-pyrid-2-yl | 4-F | S | CH₃ | H | |
| 4-CF₃ | 5-Cl-pyrid-2-yl | 4-F | S | CH₃ | CH₃ | |
| 4-CF₃ | 5-Cl-pyrid-2-yl | 4-F | O | S—N(Me)CO₂nBu | H | |
| 4-CF₃ | 5-Br-pyrid-2-yl | 4-F | O | S—N(Me)CO₂nBu | H | |
| 4-CF₃ | 5-CF₃-pyrid-2-yl | 4-F | O | S—N(Me)CO₂nBu | H | |
| 4-CF₃ | 5-Cl-pyrid-2-yl | 4-F | O | S—N(i-Pr)CO₂Et | H | |
| 4-CF₃ | 5-Br-pyrid-2-yl | 4-F | O | S—N(i-Pr)CO₂Et | H | |
| 4-CF₃ | 5-CF₃-pyrid-2-yl | 4-F | O | S—N(i-Pr)CO₂Et | H | |
| 4-CF₃ | 5-Cl-pyrid-2-yl | 4-F | O | S—N(Me)SO₂Ph | H | |
| 4-CF₃ | 5-Br-pyrid-2-yl | 4-F | O | S—N(Me)SO₂Ph | H | |
| 4-CF₃ | 5-CF₃-pyrid-2-yl | 4-F | O | S—N(Me)SO₂Ph | H | |
| 4-CF₃ | 5-Cl-pyrid-2-yl | 4-F | O | S—CO₂i-Bu | H | |
| 4-CF₃ | 5-Br-pyrid-2-yl | 4-F | O | S—CO₂i-Bu | H | |
| 4-CF₃ | 5-CF₃-pyrid-2-yl | 4-F | O | S—CO₂i-Bu | H | |
| 4-CF₃ | 5-Cl-pyrid-2-yl | 4-F | O | S—P(O)(OEt)₂ | H | |
| 4-CF₃ | 5-Br-pyrid-2-yl | 4-F | O | S—P(O)(OEt)₂ | H | |
| 4-CF₃ | 5-CF₃-pyrid-2-yl | 4-F | O | S—P(O)(OEt)₂ | H | |

Formulation and Use

The compounds of this invention will generally be used in formulation with a carrier comprising a liquid or solid diluent or an organic solvent. Useful formulations of the compounds of Formula I can be prepared in conventional ways. They include dusts, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 25–90 | 0–74 | 1–10 |
| Oil Suspensions, Emulsions, Solutions (including Emulsifiable Concentrates) | 1–50 | 40–95 | 0–35 |
| Dusts | 1–25 | 70–99 | 0–5 |
| Granules and Pellets | 1–95 | 5–99 | 0–15 |

-continued

| | Percent by Weight | | |
|---|---|---|---|
| | Active Ingredient | Diluent(s) | Surfactant(s) |
| High Strength Compositions | 90–99 | 0–10 | 0–2 |

Lower or high levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Many of the compounds of the invention are most efficacious when applied in the form of an emulsifiable concentrate mixed with a spray oil or spray oil concentrate. Although any oil can be used as a spray oil, spray oils usually have these characteristics: they are not phytotoxic to the crop sprayed, and they have appropriate viscosity. Petroleum based oils are commonly used for spraying. In some areas, crop oils are preferred such as the following:

| Common Crop Oils Used as Spray Oils | |
|---|---|
| Corn Oil | Linseed Oil |
| Cottonseed Oil | Soybean Oil |
| Coconut Oil | Sunflower Oil |
| Rapeseed Oil | Olive Oil |
| Peanut Oil | Palm Oil |
| Safflower Oil | Sesame Oil |
| Mustardseed Oil | Caster Oil |

The following oils also meet the criteria for a spray oil: mineral, fish and cod liver oil.

Spray oil concentrates comprise a spray oil together with one or more additional ingredients such as emulsifiers and wetting agents. A number of useful spray oil and spray oil concentrates can be found in "A Guide to Agricultural Spray Adjuvants Used in the United States" by Thomson, Thomson Publications, California, 1986.

Examples of useful formulations of compounds of the present invention are as follows:

EXAMPLE 7

Emulsifiable Concentrate

| | |
|---|---|
| 5-(5-chloro-2-thienyl)-1-(4-fluorophenyl)-4,5-dihydro-N-[4-(trifluoromethyl)phenyl]-1H-pyrazole-3-carboxamide | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE 8

Wettable Powder

| | |
|---|---|
| 1-(4-chlorophenyl)-5-(5-chloro-2-thienyl)-4,5-dihydro-N-[4-(trifluoromethyl)phenyl]-1H-pyrazole-3-carboxamide | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammer-mill, the material is re-blended and sifted through a 50 mesh screen.

EXAMPLE 9

Dust

| | |
|---|---|
| Wettable powder of Example 8 | 10% |
| pyrophyllite (powder) | 90% |

The wettable powder and the pyrophyllite diluent are thoroughly blended and then packaged. The product is suitable for use as a dust.

EXAMPLE 10

Granule

| | |
|---|---|
| 1-(5-chloro-2-pyridinyl)-5-(4-fluorophenyl)-4,5-dihydro-N-[4-(trifluoromethyl)phenyl]-1H-pyrazole-3-carboxamide | 10% |
| attapulgite granules (low volative matter, 0.71/0.30 mm; U.S.S. No. 25–50 sieves) | 90% |

The active ingredient is dissolved in a volatile solvent such as acetone and sprayed upon dedusted and prewarmed attapulgite granules in a double cone blender. The acetone is then driven off by heating. The granules are then allowed to cool and are packaged.

EXAMPLE 11

Granule

| | |
|---|---|
| Wettable powder of Example 8 | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE 12

Solution

| | |
|---|---|
| 1-(6-chloro-3-pyridazinyl)-5-(4-fluorophenyl)-4,5-dihydro-N-]4-(trifluoromethyl)phenyl]-1H-pyrazole-3-carboxamide | 25% |
| N-methyl-pyrrolidone | 75% |

The ingredients are combined and stirred to produce a solution suitable for direct, low volume application.

EXAMPLE 13

Aqueous Suspension

| | |
|---|---|
| 5-(5-chloro-2-thienyl)-1-(4-fluorophenyl)-4,5-dihydro-N-[4-(trifluoromethyl)phenyl]-1H-pyrazole-3-carboxamide | 40% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Oil Suspension

| | |
|---|---|
| 1-(4-chlorophenyl)-5-(5-chloro-2-thienyl)-4,5-dihydro-N-[4-(trifluoromethyl)phenyl]-1H-pyrazole-3-carboxamide | 35.0% |
| blend of polyalcohol carboxylic esters and oil soluble petroleum sulfonates | 6.0% |
| xylene range solvent | 59.0% |

The ingredients are combined and ground together in a sand mill to produce particles essentially all below 5 microns. The product can be used directly, extended with oils, or emulsified in water.

EXAMPLE 15

Bait Granules

| | |
|---|---|
| 1-(5-chloro-2-pyridinyl)-5-(4-fluorophenyl)-4,5-dihydro-N-[4-(triflyoromethyl)phenyl]-1H-pyrazole-3-carboxamide | 3.0% |
| blend of polyethoxylated nonyl-phenols and sodium dodecyl-benzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged. Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of the present invention can be mixed or formulated are:

Insecticides 3-hydroxy-N-methylcrotonamide(dimethylphosphate)ester (monocrotophos)

methylcarbamic acid, ester with 2,3-dihydro-2,2-dimethyl-7-benzofuranol (carbofuran)

O-[2,4,5-trichloro-α-(chloromethyl)benzyl]phosphoric acid, O',O'-dimethyl ester (tetrachlorvinphos)

2-mercaptosuccinic acid, diethyl ester, S-ester with thionophosphoric acid, dimethyl ester (malathion)

phosphorothioic acid, O,O-dimethyl, O-p-nitrophenyl ester (methyl parathion)

methylcarbamic acid, ester with α-naphthol (carbaryl)

methyl O-(methylcarbamoyl)thiolacetohydroxamate (methomyl)

N'-(4-chloro-o-tolyl)-N,N-dimethylformamidine (chlorodimeform)

O,O-diethyl-O-(2-isopropyl-4-methyl-6-pyrimidylphosphorothioate (diazinon)

octachlorocamphene (toxaphene)

O-ethyl O-p-nitrophenyl phenylphosphonothioate (EPN)

(S)-α-cyano-m-phenoxybenzyl(1R,3R)-3-(2,2-dibromovinyl)-2,2-dimethylcyclopropanecarboxylate (deltamethrin)

Methyl N',N'-dimethyl-N-[(methylcarbamoyl)oxy]-1-thiooxamimidate (oxamyl)

cyano(3-phenoxyphenyl)-methyl-4-chloro-α-(1-methylethyl)benzeneacetate (fenvalerate)

(3-phenoxyphenyl)methyl(±)-cis,trans-3-(2,2-dichloroethenyl)-2,2-dimethylcyclopropanecarboxylate (permethrin)

α-cyano-3-phenoxybenzyl 3-(2,2-dichlorovinyl)-2,2-dimethylcyclopropane carboxylate (cypermethrin)

O-ethyl-S-(p-chlorophenyl)ethylphosphonodithioate (profenofos)

phosphorothiolothionic acid, O-ethyl-O-[4-(methylthio)phenyl]-S-n-propyl ester (sulprofos).

Additional insecticides are listed hereafter by their common names: triflumuron, diflubenzuron, methoprene, buprofezin, thiodicarb, acephate, azinphos-methyl, chlorpyrifos, dimethoate, fonophos, isofenphos, methidathion, methamidiphos, monocrotophos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides

S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Bactericides tribasic copper sulfate
streptomycin sulfate.

Acaricides senecioic acid, ester with 2-sec-butyl-4,6-dinitrophenol (binapacryl)
6-methyl-1,3-dithiolo[4,5-$\beta$]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
bisclofentezin.

Biological

*Bacillus thuringiensis*
Avermectin B.

Utility

The compounds of the present invention exhibit activity against a wide spectrum of foliar and soil inhabiting insects. Those skilled in the art will recognize that not all compounds are equally effective against all insects, but the compounds of this invention display activity against economically important pest species, such as grasshoppers and cockroaches; thrips; hemipterans; plant bugs (Miridae), such as tarnished plant bug, lace bugs (Tingidae), seed bugs (Lygaeidae) such as cinch bugs, stink bugs (Pentatomidae), leaf-footed bugs (Coreidae), such as squash bug, and red bugs and stainers (Pyrrhocoridae) such as cotton stainer; also homopterans such as whiteflies, aphids such as the green peach aphid, greenbug and cotton aphid, leafhoppers, spittlebugs and plant hoppers such as aster leafhopper, potato leafhopper and rice planthoppers, psyllids such as pear psylla, scales (coccids and diaspidids) and mealybugs; coleopterans including weevils, such as boll weevil and rice water weevil, grain borers, chrysomellid beetles, such as Colorado potato beetle, flea beetles and other leaf beetles, coccinellid beetles such as Mexican bean beetle, and soil insects such as southern corn rootworm and wireworm; lepidopterous larvae including noctuids such as fall armyworm, beet armyworm, other *Spodoptera* spp., *Heliothis virescens*, *Heliothis zea*, cabbage looper, green cloverworm, velvetbean caterpillar, cotton leafworm, black cutworm, and other noctuid cutworms and including pyralids such as European corn borer, navel orangeworm, and stalk/stem borers and including tortricids like codling moth and grape berry moth as well as other lepidopterous larvae, such as pink bollworm and diamondback moth; and dipterans such as leafminers, soil maggots, midges, tephritid fruit flies. The specific species, for which control is exemplified below, are: fall armyworm, *Spodoptera frugiperda*; tobacco budworm, *Heliothis virescens*; boll weevil, *Anthonomus grandis*; European corn borer, *Ostrinia nubilalis*; southern corn rootworm, *Diabrotica undecimpunctata howardi*; aster leafhopper, *Macrosteles fascifrons*. The pest control afforded by the compounds of the present invention is not limited, however, to these species.

Application

Insects are controlled and agricultural crops are protected by applying one or more of the Formula I compounds of this invention, in an effective amount, to the locus of infestation, to the area to be protected, or directly on the pests to be controlled. A preferred method of application is by spraying with spray equipment that distributes the compound on the foliage, in the soil, or to the plant part that is infested or needs to be protected. Alternatively granular formulations of these compounds can be applied to soil or foliage or, optionally, incorporated into the soil. Either aerial or ground application can be used.

The pyrazoline compound(s) of this invention can be applied directly, but most often application will be of a formulation comprising one or more compounds of this invention, in an agriculturally suitable carrier or diluent. A most preferred method of application involves spraying a water dispersion or refined oil solution of the compounds. Combinations with spray oils and spray oil concentrations often enhance the efficacy of the compounds of Formula I.

The rate of application of the Formula I compounds required for effective control will depend on such factors as the species of insect to be controlled, the pest's life stage, its size, its loction, the host crop, time of year of application, ambient moisture, temperature conditions, and the like. In general, application rates of 0.05 to 2 kg of active ingredient per hectare are sufficient to provide effective control in large scale field operations under normal circumstances, but as little as 0.001 kg/hectare may be sufficient or as much as 8 kg/hectare may be required, depending upon the factors listed above. The addition of a compound such as piperonyl butoxide, can enhance the insecticidal activity of many of the compounds of Formula I.

The following examples demonstrate the control efficacy of compounds of Formula I on specific insect pests wherein Compounds 1 through 31 are described in Table 6.

TABLE 6
Compound 1
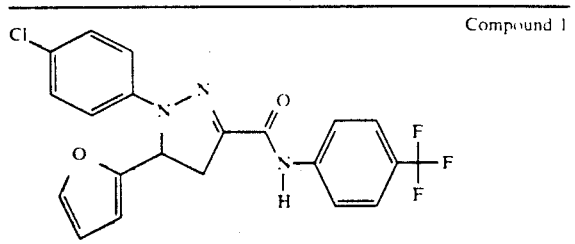
Compound 2
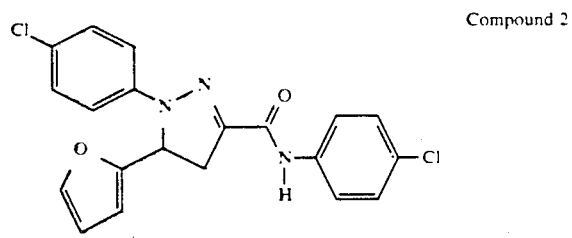
Compound 3
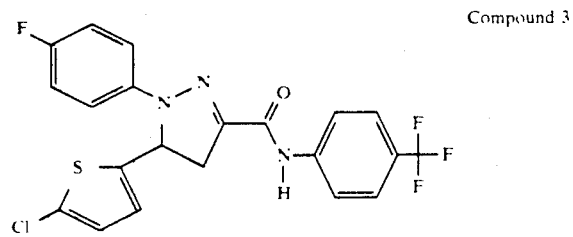
Compound 4
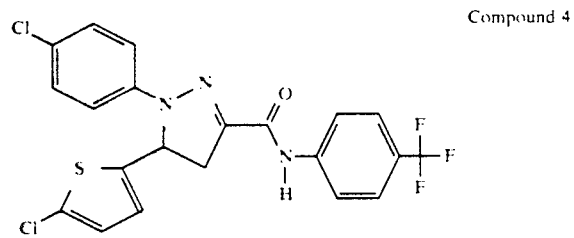
Compound 5
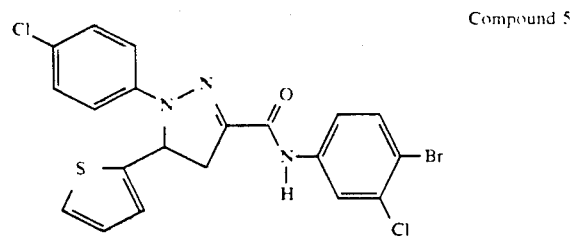
Compound 6
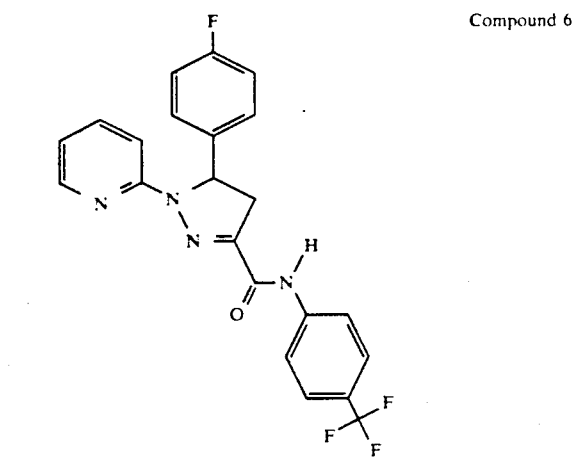
TABLE 6-continued
Compound 7
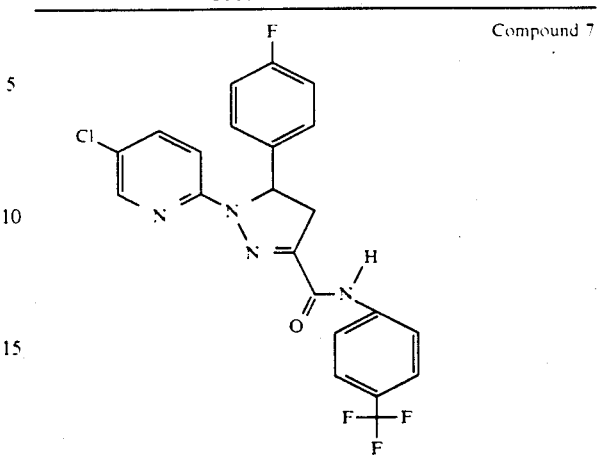
Compound 8
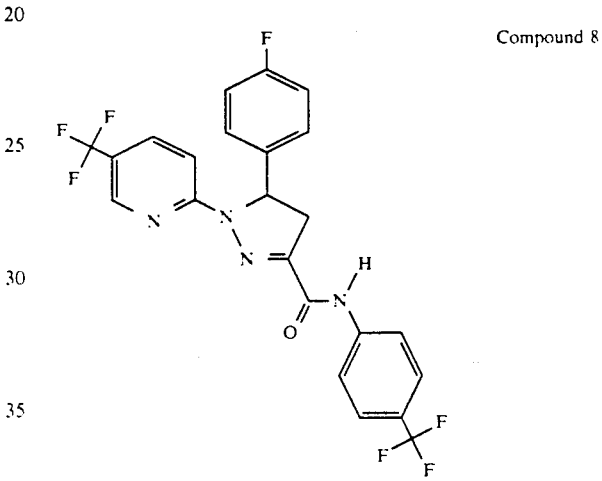
Compound 9
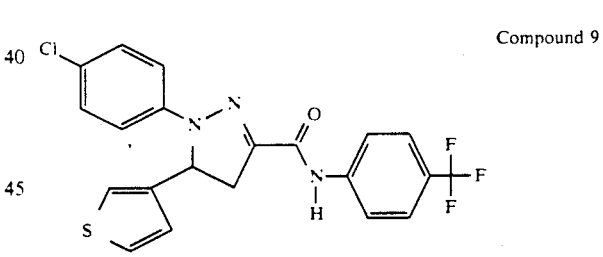
Compound 10
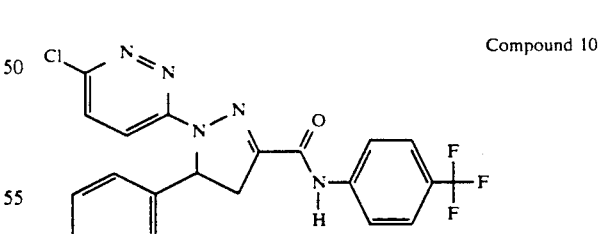
Compound 11
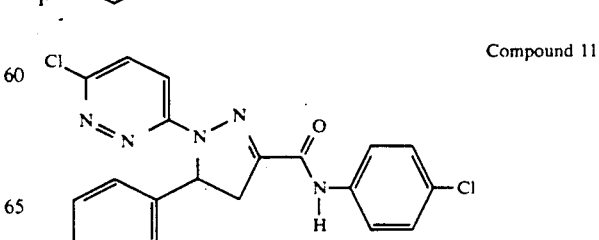

TABLE 6-continued
Compound 12
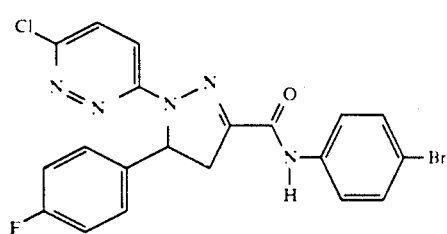
Compound 17
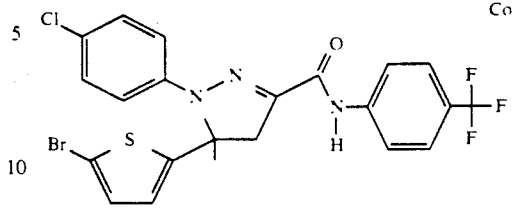
Compound 13
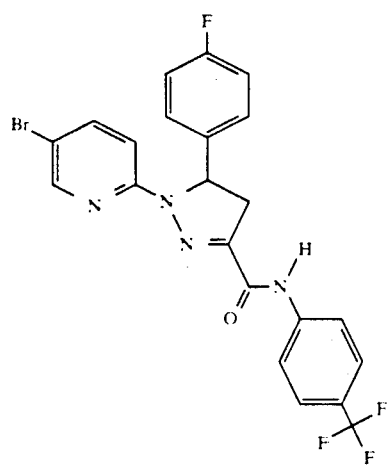
Compound 18
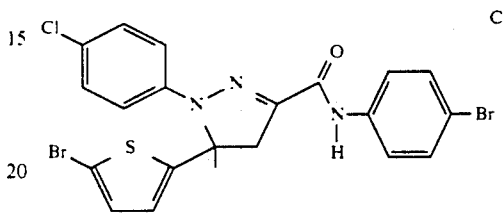
Compound 14
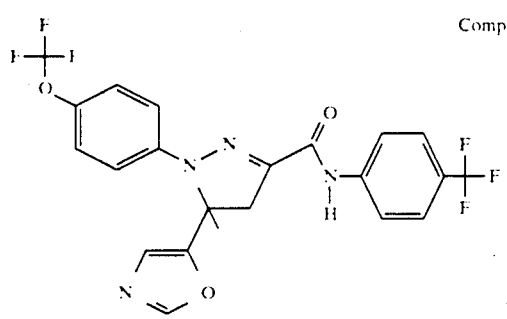
Compound 19
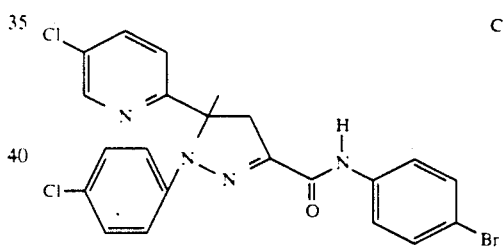
Compound 15
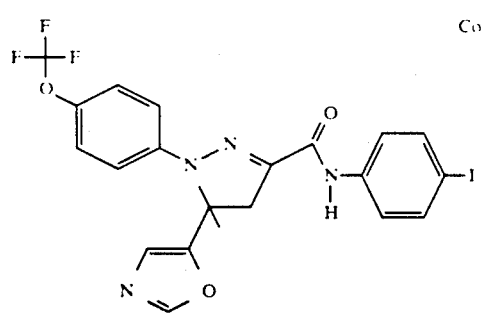
Compound 20
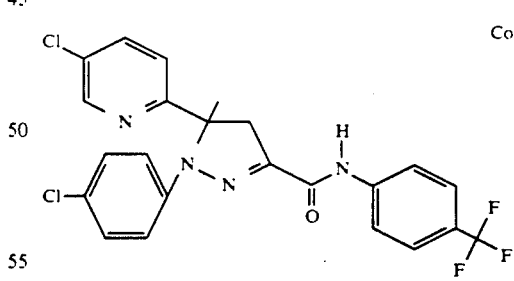
Compound 16
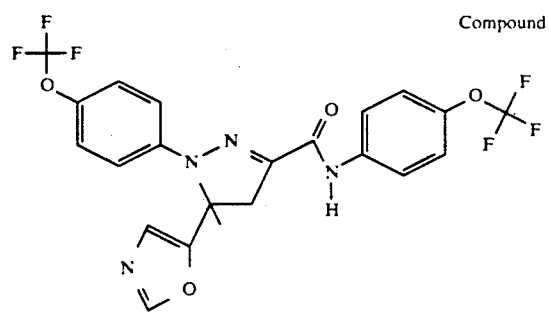
Compound 21
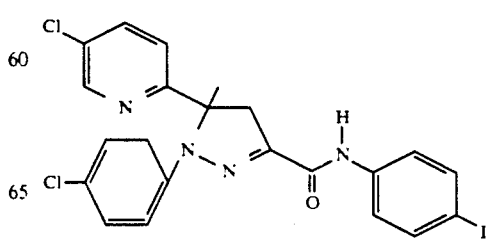
Compound 22

TABLE 6-continued
Compound 23
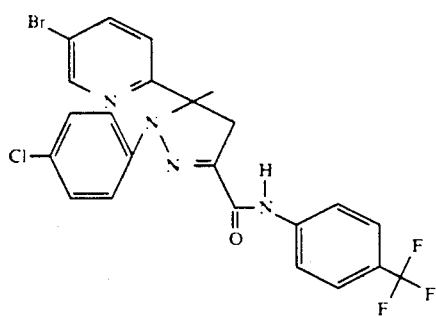
Compound 24
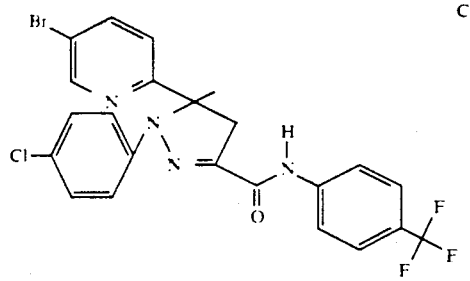
Compound 25
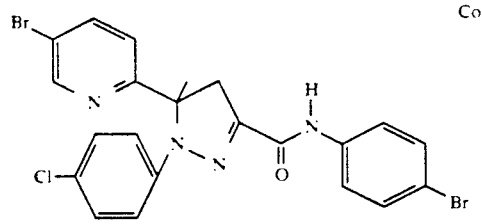
Compound 26
Compound 27
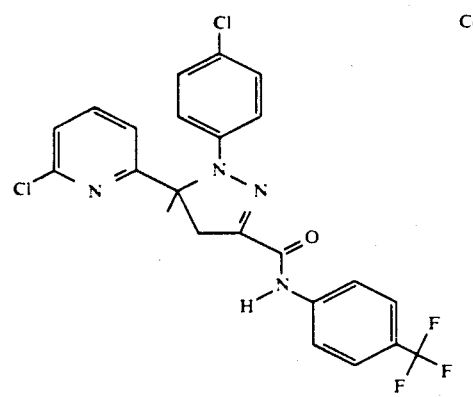
TABLE 6-continued
Compound 28
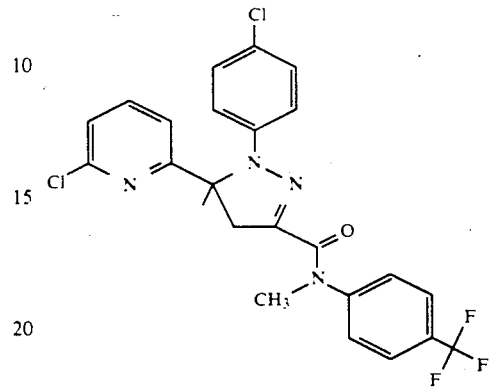
Compound 29
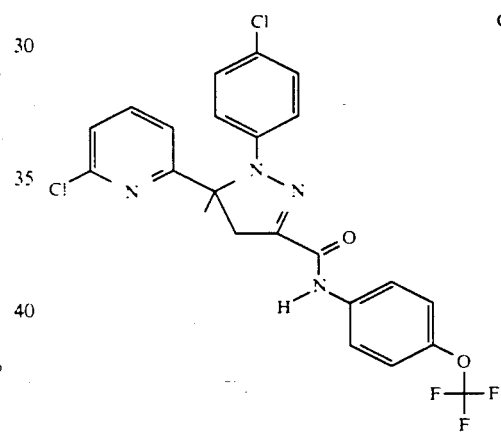
Compound 30
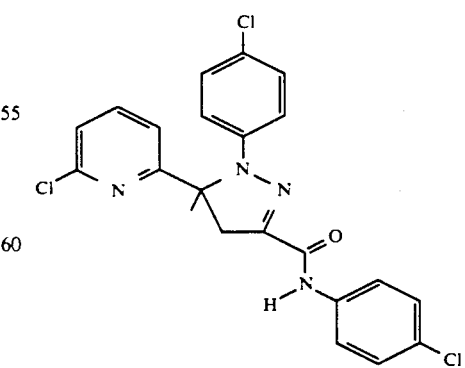

TABLE 6-continued

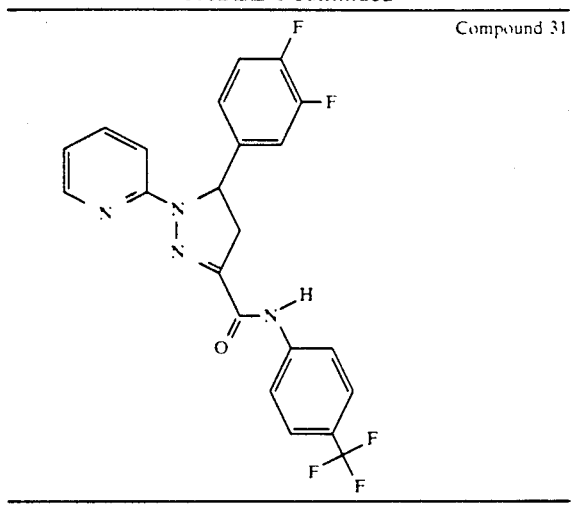

Compound 31

EXAMPLE 16

Fall Armyworm

Test units, each consisting of an 8-ounce plastic cup containing a layer of wheat germ diet, approximately 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed onto the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time readings were taken. Of the compounds tested on fall armyworm, the following resulted in greater than or equal to 80% mortality: 1, 3, 4, 5, 6, 7, 8, 10, 11, 12, 14, 15, 16, 17, 18, 19, 20, 21, 22, 23, 24, 25, 26, 27, 28, 29, 30 and 31.

EXAMPLE 17

Tobacco Budworm

The test procedure of Example 16 was repeated for efficacy against third-instar larvae of the tobacco budworm (*Heliothis virescens*) except that mortality was assessed at 48 hours. Of the compounds tested on tobacco budworm, the following resulted in greater than or equal to 80% mortality: 7, 8, 10, 11, 12, 13, 14, 17, 19, 20, 21, 22, 23, 24, 25, 26, 27, 28 and 29.

EXAMPLE 18

European Corn Borer

Test units, each consisting of an 8-ounce plastic cup containing one-inch square of wheat germ/soyflour diet, were prepared. Five third-instar larvae of the European corn borer (*Ostrinia nubilalis*) were placed into each cup. Sets of three test units were sprayed as described in Example 16 with individual solutions of the test compounds. The cups were then covered and held at 27° C. and 50% relative humidity for 48 hours, after which time mortality readings were taken. Of the compounds tested on European corn borer, the following resulted in greater than or equal to 80% mortality: 1, 3, 4, 6, 7, 8, 9 and 10.

EXAMPLE 19

Southern Corn Rootworm

Test units, each consisting of an 8-ounce plastic cup containing 1 sprouted corn seed (*Zea mays*), were prepared. Sets of three test units were sprayed as described in Example 16 with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested on southern corn rootworm, the following resulted in greater than or equal to 80% mortality: 4, 7, 11, 13, 15, 19, 21, 22, 23, 24, 25, 26, 27, 28, 29 and 31.

EXAMPLE 20

Boll Weevil

Five adult boll weevils (*Anthonomus grandis*) were placed into each of a series of 9-ounce cups. The test procedure employed was then otherwise the same as in Example 16 with three cups per treatment. Mortality readings were taken 48 hours after treatment. Of the compounds tested on boll weevil, the following resulted in greater than or equal to 80% mortality: 1, 2, 7, 9, 10, 27, 28, 29 and 30.

EXAMPLE 21

Aster Leafhopper

Test units were prepared from a series of 12-ounce cups, each containing oat (*Avena sativa*) seedlings in a 1-inch layer of sterilized soil. Sets of three test units were sprayed as described in Example 16 with individual solutions of the test compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested on aster leafhopper, the following resulted in greater than or equal to 80% mortality: 7, 8, 19, 20, 21, 23, 24 and 27.

The embodiments of the invention in which an exclusive property or privilege is claimed are defined as follows:

1. A compound of the formula

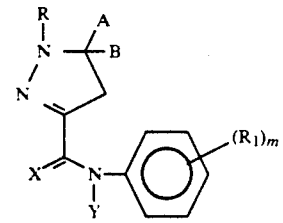

wherein:
X is O or S;
Y is selected from the group H, $C_1$ to $C_4$ alkyl, $C_2$ to $C_4$ alkoxyalkyl, $C_1$ to $C_4$ alkylthio, $C_1$ to $C_4$ haloalkylthio, SX', phenylthio, or phenylthio substituted with 1 to 3 substituents independently selected from W, $C_2$ to $C_4$ alkoxycarbonyl, C(O)H, $C_2$ to $C_4$ alkylcarbonyl and $C_2$ to $C_4$ haloalkylcarbonyl;

A is selected from the group H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$, $C(S)SR_3$;

B is selected from the group H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_2$ to $C_6$ alkenyl, $C_2$ to $C_6$ alkynyl, $C_2$ to $C_6$ alkoxycarbonyl, phenyl, phenyl substituted with 1 to 3 substituents independently selected from W, benzyl and benzyl substituted with 1 to 3 substituents independently selected from W;

W is selected from the group halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl and $C_1$ to $C_2$ haloalkylsulfonyl;

R is

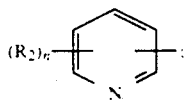

$R_1$, $R_2$ and $R_5$ are independently selected from the group $R_3$, halogen, CN, $N_3$, SCN, $NO_2$, $OR_3$, $SR_3$, $S(O)R_3$, $S(O)_2R_3$, $OC(O)R_3$, $OS(O)_2R_3$, $CO_2R_3$, $C(O)R_3$, $C(O)NR_3R_4$, $S(O)_2NR_3R_4$, $NR_3R_4$, $NR_4C(O)R_3$, $OC(O)NHR_3$, $NR_4C(O)NHR_3$, $NR_4S(O)_2R_3$;

$R_3$ is selected from the group H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, $C_2$ to $C_4$ haloalkynyl, $C_2$ to $C_4$ alkoxyalkyl, $C_2$ to $C_4$ alkylthioalkyl, $C_1$ to $C_4$ nitroalkyl, $C_1$ to $C_4$ cyanoalkyl, $C_3$ to $C_6$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H or $C_1$ to $C_4$ alkyl;

X' is

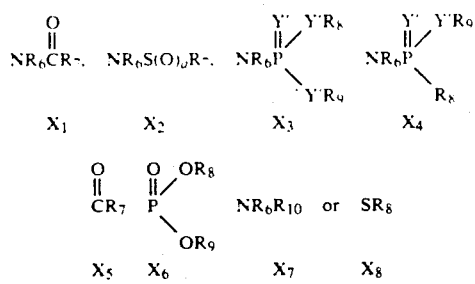

$R_6$ and $R_{10}$ are independently selected from $C_1$ to $C_6$ alkyl, $C_1$-$C_6$ haloalkyl, $C_3$-$C_6$ cycloalkyl, $C_4$-$C_7$ cycloalkylalkyl, $C_2$ to $C_6$ cyanoalkyl, $C_2$ to $C_6$ alkoxyalkyl, $C_3$ to $C_8$ alkoxycarbonylalkyl, $C_4$ to $C_8$ dialkylaminocarbonylalkyl, phenyl optionally substituted by 1 to 2 substituents selected from W, benzyl optionally substituted by 1 to 2 substituents selected from W, and phenethyl optionally substituted by 1 to 2 substituents selected from W;

R is F, $C_1$-$C_{20}$ alkyl, $C_1$-$C_6$ haloalkyl, $C_2$-$C_8$ dialkylamino, phenyl optionally substituted by 1 to 2 substituents selected from W, or $R_7$ is $C_1$-$C_{20}$ alkoxy, $C_1$-$C_4$ alkoxy substituted by cyano, nitro, $C_1$-$C_4$ alkoxy, $C_4$-$C_8$ alkoxyalkoxy, $C_1$-$C_2$ alkylthio, $C_2$-$C_3$ alkoxycarbonyl, $C_3$-$C_5$ dialkylaminocarbonyl, phenyl or 1 to 6 halogens, or $R_7$ is phenoxy optionally substituted by 1 to 2 substituents selected from W;

$R_8$ and $R_9$ are independently selected from $C_1$-$C_4$ alkyl, $C_2$-$C_4$ haloalkyl or phenyl optionally substituted by 1 to 2 substituents selected from W;

a is 0 to 2;

Y' is O or S;

m is 1 to 3;

n is 0 to 3; and p is 0 to 3.

2. A compound according to claim 1 wherein:

X is O;

Y is H, $CH_3$, $SCH_3$, $SCCl_3$, $SC_6H_5$, 2-$(NO_2)C_6H_4S$, $C(O)CH_3$, C(O)H, $C(O)CF_3$, $CO_2CH_3$, $CO_2C_2H_5$ or SX';

X' is $X_1$, $X_2$, $X_3$, $X_4$, $X_5$ or $X_7$;

$R_6$ and $R_{10}$ are independently selected from $C_1$-$C_6$ alkyl, $C_1$-$C_6$ haloalkyl, $C_5$-$C_6$ cycloalkyl, $C_3$-$C_8$ alkoxycarbonylalkyl, phenyl, benzyl or phenethyl each optionally substituted with W;

$R_8$ and $R_9$ are independently selected from $C_1$-$C_3$ alkyl and phenyl;

a is 2;

$R_3$ is $C_1$ to $C_4$ alkyl, $C_1$ to $C_2$ haloalkyl, $C_2$ to $C_4$ alkenyl, $C_2$ to $C_4$ haloalkenyl, propargyl, phenyl, benzyl; or phenyl or benzyl substituted with one of F, Cl, Br, $CF_3$, $OCF_2H$, $OCF_3$ or $NO_2$;

B is H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_1$ to $C_6$ alkenyl, $C_1$ to $C_6$ alkynyl or $C_2$ to $C_6$ alkoxycarbonyl;

n is 0 to 2; and m is 1 to 2.

3. A compound according to claim 2 wherein:

$R_1$ is halogen, CN, SCN, $NO_2$, $R_3$, $OR_3$, $SR_3$, $S(O)_2R_3$, $CO_2R_3$ or $C(O)R_3$;

$R_2$ is halogen, CN, SCN, $NO_2$, $R_3$, $OR_3$, $SR_3$, $S(O)_2R_3$, $OC(O)R_3$, $OS(O)_2R_3$, $CO_2R_3$, $C(O)R_3$, $C(O)NR_3R_4$, $S(O)_2NR_3R_4$ or $NR_3R_4$;

$R_3$ is $C_1$ to $C_4$ alkyl, $C_1$ to $C_2$ haloalkyl, $C_2$ to $C_4$ alkenyl, $C_2$ to $C_4$ haloalkenyl or propargyl;

$R_4$ is H or $C_1$ to $C_2$ alkyl;

W is halogen, CN, $CO_2CH_3$, $C(O)NHCH_3$, $C(O)N(CH_3)_2$, $NO_2$, $CH_3$, $CF_3$, $OCH_3$, $OCF_2H$, $OCF_2CF_2H$, $SCH_3$, $SCF_2H$, $SCF_2CF_2H$ or $S(O)_2CH_3$;

B is H, $C_1$ to $C_4$ alkyl, $C_1$ to $C_4$ haloalkyl, or $C_3$ to $C_4$ alkenyl.

4. A compound according to claim 3 wherein:

Y is H, $CH_3$, $C(O)CH_3$, $CO_2CH_3$ or SX';

X' is $X_1$, $X_2$, $X_3$ or $X_5$;

$R_6$ is $C_1$-$C_4$ alkyl, $CF_3$, cyclohexyl, phenyl optionally substituted by W, or benzyl optionally substituted by W;

$R_7$ is F, $C_1$-$C_{12}$ alkyl, $C_1$-$C_6$ haloalkyl, phenyl or phenoxy each optionally substituted by W, $C_1$-$C_{12}$ alkoxy, dimethylamino or $C_1$-$C_4$ alkoxy substituted with $NO_2$, $C_2$-$C_4$ alkoxy or 1-6 halogens;

m is 1 or 2 and one substituent is in the 4-position of the phenyl ring;

n is 0, 1 or 2 and one substituent is in the 4-position of the phenyl ring;

$R_1$ is F, Cl, Br, $CF_3$, $OCF_2H$, $OCF_3$, CN;

$R_2$ is F, Cl, Br, CN, $NO_2$, $CF_3$, $CH_3$, $OCH_3$, $OCF_2H$, $OCF_3$, $SCH_3$, $SCF_2H$, $S(O)_2CH_3$ or $N(CH_3)_2$; and B is H or $CH_3$.

5. A compound according to claim 1 wherein:

A is H, $C_1$ to $C_6$ alkyl, phenyl, phenyl substituted by $(R_5)_p$, $CO_2R_3$, $C(O)R_3$, $C(O)NR_3R_4$, $C(S)NR_3R_4$, $C(S)R_3$ or $C(S)SR_3$.

6. A compound according to claim 5 wherein:

X is O;

Y is H, $CH_3$, $SCH_3$, $SCCl_3$, $SC_6H_5$, $2-(NO_2)C_6H_4S$, $C(O)CH_3$, $C(O)H$, $C(O)CF_3$, $CO_2CH_3$ or $CO_2C_2H_5$;

$R_3$ is $C_1$ to $C_4$ alkyl, $C_1$ to $C_2$ haloalkyl, $C_2$ to $C_4$ alkenyl, $C_2$ to $C_4$ haloalkenyl, propargyl, phenyl, benzyl, or phenyl or benzyl substituted with one of F, Cl, Br, $CF_3$, $OCF_2H$, $OCF_3$ or $NO_2$;

m is 1 to 2; and p is 0 to 2.

7. A compound according to claim 6 wherein:

$R_1$ is halogen, CN, SCN, $NO_2$, $R_3$, $OR_3$, $SR_3$, $S(O)_2R_3$, $CO_2R_3$ or $C(O)R_3$;

$R_3$ is $C_1$ to $C_4$ alkyl, $C_1$ to $C_2$ haloalkyl, $C_2$ to $C_4$ alkenyl, $C_2$ to $C_4$ haloalkenyl or propargyl;

$R_4$ is H or $C_1$ to $C_2$ alkyl;

$R_5$ is halogen, CN, SCN, $NO_2$, $R_3$, $OR_3$, $SR_3$, $S(O)_2R_3$, $OC(O)R_3$, $OS(O)_2R_3$, $CO_2R_3$, $C(O)R_3$, $C(O)NR_3R_4$, $S(O)_2NR_3R_4$ or $NR_3R_4$;

W is halogen, CN, $CO_2CH_3$, $C(O)NHCH_3$, $C(O)N(CH_3)_2$, $NO_2$, $CH_3$, $CF_3$, $OCH_3$, $OCF_2H$, $OCF_2CF_2H$, $SCH_3$, $SCF_2H$, $SCF_2CF_2H$ or $S(O)_2CH_3$;

A is $C_1$ to $C_4$ alkyl, phenyl, phenyl substituted with $(R_5)_p$, $CO_2R_3$, $C(O)R_3$, $C(O)NR_3R_4$ or $C(O)NR_4$ phenyl said phenyl optionally substituted with F, Cl, Br, $CF_3$, $OCF_2H$, $OCF_3$ or $NO_2$;

B is H, $C_1$ to $C_4$ alkyl, $C_1$ to $C_4$ haloalkyl, or $C_3$ to $C_4$ alkenyl; and $R_6$ is H or $C_1$ to $C_2$ alkyl.

8. A compound according to claim 7 wherein:

Y is H, $CH_3$, $C(O)CH_3$ or $CO_2CH_3$;

$R_1$ is F, Cl, Br, $CF_3$, $OCF_2H$, $OCF_3$, CN;

$R_5$ is F, Cl, Br, CN, $NO_2$, $CF_3$, $CH_3$, $OCH_3$, $OCF_2H$, $OCF_3$, $SCH_3$, $SCF_2H$, $S(O)_2CH_3$, $S(O)_2CF_2H$, $CO_2CH_3$, $C(O)NHCH_3$, $C(O)N(CH_3)_2$, $S(O)_2N(CH_3)_2$ or $N(CH_3)_2$;

A is phenyl substituted with $(R_5)_p$;

B is H or $CH_3$;

m is 1 or 2 and one substituent is in the 4-position of the phenyl ring; and p is 1 or 2 and one substituent is in the 3 or 4-position of the phenyl ring.

9. A compound according to claim 7 wherein:

Y is H, $CH_3$, $C(O)CH_3$ or $CO_2CH_3$;

$R_1$ is F, Cl, Br, $CF_3$, $OCF_2H$, $OCF_3$, CN;

A is $CO_2CH_3$, $CO_2C_2H_5$, $C(O)NHCH_3$ or $C(O)N(CH_3)_2$;

B is $CH_3$; and m is 1 or 2 and one substituent is in the 4-position of the phenyl ring.

10. A compound according to claim 8: 1-(5-chloro-2-pyridinyl)-5-(4-fluorophenyl)-4,5-dihydro-N-[4-(trifluoromethyl)phenyl]-1H-pyrazole-3-carboxamide.

11. A compound according to claim 8: 1-(5-bromo-2-pyridinyl)-5-(4-fluorophenyl)-4,5-dihydro-N-[4-(trifluoromethyl)phenyl]-1H-pyrazole-3-carboxamide.

12. A composition comprising an insecticidally effective amount of a compound according to any one of claims 1, 2 to 9, 10 and 11 and an agriculturally suitable carrier therefor.

13. A method of controlling insects comprising contacting them or their environment with an effective amount of a compound according to any one of claims 1, 2 to 9, 10 and 11.

* * * * *